United States Patent
Le Gette et al.

(10) Patent No.: US 9,066,829 B2
(45) Date of Patent: Jun. 30, 2015

(54) EAR WARMER WITH FABRIC MEMBER

(75) Inventors: Brian E. Le Gette, Baltimore, MD (US);
David L. Reeb, Columbia, MD (US);
Alan S. Tipp, Ellicott City, MD (US);
Justin Saul Werner, Millersville, MD (US)

(73) Assignee: 180s, Inc., Baltimore, MD (US)

( * ) Notice: Subject to any disclaimer, the term of this patent is extended or adjusted under 35 U.S.C. 154(b) by 1248 days.

(21) Appl. No.: 12/168,027

(22) Filed: Jul. 3, 2008

(65) Prior Publication Data

US 2008/0307565 A1 Dec. 18, 2008

Related U.S. Application Data

(62) Division of application No. 10/638,476, filed on Aug. 12, 2003, now Pat. No. 7,650,649.

(51) Int. Cl.
*A42B 1/06* (2006.01)
*A61F 11/14* (2006.01)

(52) U.S. Cl.
CPC ...................................... *A61F 11/14* (2013.01)

(58) Field of Classification Search
USPC .............................................. 2/208, 209, 174
See application file for complete search history.

(56) References Cited

U.S. PATENT DOCUMENTS

| 138,894 A * | 5/1873 | Isidor ................................. 2/209 |
|---|---|---|
| 139,831 A * | 6/1873 | Stone ................................. 2/209 |
| 170,942 A | 12/1875 | Edgar |
| 183,359 A | 10/1876 | Abbott |
| 184,006 A | 11/1876 | Edgar |
| 185,506 A | 12/1876 | Edgar |
| 188,292 A * | 3/1877 | Greenwood .................... 2/209 |
| 190,720 A | 5/1877 | Kleinert |
| 227,364 A | 5/1880 | Kleinert |
| 315,233 A | 4/1885 | Britton |
| 358,718 A | 3/1887 | Basch |
| 359,425 A | 3/1887 | Britton |
| 359,612 A | 3/1887 | Kleinert |
| 360,985 A | 4/1887 | Basch |

(Continued)

FOREIGN PATENT DOCUMENTS

| CA | 2180036 | 1/1997 |
|---|---|---|
| CH | 294003 | 1/1954 |

(Continued)

OTHER PUBLICATIONS

Advertisement: The "PODZ" ear warming eye glass retainer, Shred Alert Products of Hood River, Oregon, 5 pgs.

(Continued)

*Primary Examiner* — Shaun R Hurley
*Assistant Examiner* — Andrew W Sutton
(74) *Attorney, Agent, or Firm* — Cooley LLP

(57) ABSTRACT

An ear warmer comprises a frame and a fabric member. The frame has an ear portion and a band portion. The ear portion of the frame includes a first side and a second side opposite the first side. The first side of the ear portion defines an interior portion of an opening. The second side of the ear portion defines an exterior portion of the opening. The fabric member includes at least its own ear portion coupled to the ear portion of the frame. The ear portion of the fabric member covers the interior portion of the opening in substantially its entirety and covers less than an entirety of the exterior portion of the opening.

22 Claims, 40 Drawing Sheets

(56) References Cited

U.S. PATENT DOCUMENTS

| | | | |
|---|---|---|---|
| 365,061 A | 6/1887 | Friedman | |
| 375,594 A | 12/1887 | Basch | |
| 381,559 A | 4/1888 | Kleinert et al. | |
| 486,725 A | 11/1892 | Mellor | |
| 503,703 A | 8/1893 | Kleinert | |
| 516,135 A | 3/1894 | Thamm | |
| 529,176 A | 11/1894 | Kleinert | |
| 548,738 A | 10/1895 | Ballard | |
| 758,680 A * | 5/1904 | Otte | 2/209 |
| 804,731 A * | 11/1905 | Keller | 2/209 |
| 836,087 A | 11/1906 | Callahan | |
| 869,741 A | 10/1907 | Seitzman | |
| 932,487 A | 8/1909 | Melio | |
| 953,623 A | 3/1910 | Keller | |
| 1,149,806 A * | 8/1915 | Basch | 2/209 |
| 1,167,368 A | 1/1916 | Adams-Randall | |
| 1,179,473 A | 4/1916 | Taylor | |
| 1,274,842 A | 8/1918 | Basch | |
| 1,326,875 A | 12/1919 | Miller | |
| 1,395,864 A | 11/1921 | Pape | |
| 1,398,958 A | 12/1921 | Basch | |
| 1,438,171 A * | 12/1922 | Delson | 2/172 |
| 1,567,105 A | 12/1925 | Bohlman | |
| 1,577,183 A | 3/1926 | Dowiarz | |
| 1,628,483 A | 5/1927 | Wiegand et al. | |
| 1,873,864 A | 8/1932 | Ely | |
| 1,945,110 A | 1/1934 | Gordon | |
| 1,988,880 A | 1/1935 | Strouse | |
| 2,070,216 A | 2/1937 | Rosenberg | |
| 2,120,189 A | 6/1938 | Reinemer | |
| 2,149,383 A * | 3/1939 | Bean | 2/209 |
| 2,184,996 A * | 12/1939 | Joseph | 2/209 |
| 2,216,954 A * | 10/1940 | McDonough | 2/209 |
| 2,241,736 A | 5/1941 | Reinemer | |
| 2,246,031 A | 6/1941 | Baritz et al. | |
| 2,314,782 A | 3/1943 | Goretsky | |
| 2,333,392 A | 11/1943 | Rosenzweig | |
| 2,378,398 A | 6/1945 | Fiedler | |
| 2,405,326 A | 8/1946 | Plotsky | |
| 2,420,245 A | 5/1947 | Hurst | |
| 2,437,049 A | 3/1948 | Salisbury et al. | |
| 2,439,289 A | 4/1948 | Fanslow | |
| 2,447,078 A | 8/1948 | Maxant | |
| 2,464,331 A * | 3/1949 | Mason | 2/171 |
| 2,532,852 A | 12/1950 | Oaks | |
| 2,572,746 A | 10/1951 | Mougel | |
| 2,582,907 A | 1/1952 | Kaufmann | |
| 2,586,644 A | 2/1952 | Gilbert | |
| 2,609,544 A | 9/1952 | Berg | |
| 2,615,169 A * | 10/1952 | Maxant | 2/209 |
| 2,651,046 A | 9/1953 | Berg | |
| 2,671,221 A | 3/1954 | Triplett | |
| 2,678,999 A | 5/1954 | Norris | |
| 2,717,930 A | 9/1955 | Hintz | |
| 2,738,514 A | 3/1956 | Gondell | |
| 2,776,436 A | 1/1957 | Berg | |
| 2,782,423 A | 2/1957 | Simon et al. | |
| 2,858,544 A | 11/1958 | Roth | |
| 2,899,683 A | 8/1959 | Wadsworth et al. | |
| 2,946,860 A | 7/1960 | Jansen et al. | |
| 3,087,028 A | 4/1963 | Bonnin | |
| 3,104,398 A | 9/1963 | Palmaer | |
| 3,112,493 A * | 12/1963 | Greenberg | 2/209 |
| 3,119,119 A * | 1/1964 | Millinger et al. | 2/209 |
| 3,119,904 A | 1/1964 | Anson | |
| 3,156,923 A | 11/1964 | Timm | |
| 3,235,882 A | 2/1966 | Coleman | |
| 3,249,949 A * | 5/1966 | Rosenberg et al. | 2/209 |
| 3,308,480 A | 3/1967 | Elder | |
| 3,311,713 A | 3/1967 | Knuebel | |
| 3,440,663 A | 4/1969 | Beguin | |
| 3,447,160 A | 6/1969 | Teder | |
| 3,505,684 A | 4/1970 | Hutchinson et al. | |
| 3,509,580 A | 5/1970 | Rubenstein et al. | |
| 3,686,691 A | 8/1972 | Anderson | |
| 3,721,993 A | 3/1973 | Lonnstedt | |
| 3,728,741 A | 4/1973 | Lepor | |
| 3,787,899 A | 1/1974 | Krawagna | |
| 3,815,155 A | 6/1974 | Davison et al. | |
| 3,841,325 A | 10/1974 | Pickard | |
| 3,944,018 A | 3/1976 | Satory | |
| 4,048,453 A | 9/1977 | Seidel | |
| 4,133,053 A | 1/1979 | Lundin | |
| 4,277,847 A | 7/1981 | Florio | |
| 4,349,081 A | 9/1982 | Pepple | |
| D266,417 S | 10/1982 | Perez | |
| 4,391,000 A | 7/1983 | Lonnstedt | |
| 4,404,434 A | 9/1983 | Pelt et al. | |
| 4,409,442 A | 10/1983 | Kamimura | |
| 4,445,005 A | 4/1984 | Furuhashi | |
| 4,455,457 A | 6/1984 | Akira | |
| 4,463,223 A | 7/1984 | Yamanoi et al. | |
| 4,471,496 A | 9/1984 | Gardner, Jr. et al. | |
| 4,486,903 A | 12/1984 | Krystal | |
| 4,499,593 A | 2/1985 | Antle | |
| 4,516,274 A | 5/1985 | Buckland | |
| 4,542,803 A | 9/1985 | Houng | |
| 4,546,215 A | 10/1985 | Ferraro | |
| 4,571,746 A | 2/1986 | Gorike | |
| 4,609,786 A | 9/1986 | Omoto et al. | |
| 4,615,185 A | 10/1986 | Bollinger | |
| 4,633,530 A | 1/1987 | Satterfield | |
| 4,654,898 A | 4/1987 | Ishikawa | |
| 4,660,229 A | 4/1987 | Harris | |
| 4,669,129 A | 6/1987 | Chance | |
| 4,670,911 A | 6/1987 | Dunford | |
| 4,682,374 A | 7/1987 | Geiser | |
| 4,713,843 A | 12/1987 | Duncan | |
| 4,727,599 A | 2/1988 | Rappaport et al. | |
| 4,747,145 A | 5/1988 | Wiegel | |
| 4,776,042 A | 10/1988 | Hanson et al. | |
| 4,776,044 A | 10/1988 | Makins | |
| 4,783,822 A | 11/1988 | Toole et al. | |
| 4,791,684 A | 12/1988 | Schwartz | |
| 4,796,307 A | 1/1989 | Vantine | |
| 4,802,245 A | 2/1989 | Miano | |
| 4,805,239 A | 2/1989 | Ciago | |
| D301,477 S | 6/1989 | Storyk | |
| 4,845,751 A | 7/1989 | Schwab | |
| 4,850,055 A * | 7/1989 | Hwang | 2/209 |
| 4,858,248 A | 8/1989 | Goldsmith et al. | |
| 4,864,619 A | 9/1989 | Spates | |
| 4,872,219 A | 10/1989 | Duncan | |
| 4,907,266 A | 3/1990 | Chen | |
| 4,918,757 A | 4/1990 | Janssen et al. | |
| 4,930,148 A | 5/1990 | Lee | |
| 4,969,069 A | 11/1990 | Eichost | |
| 4,982,451 A | 1/1991 | Graham | |
| 5,003,589 A | 3/1991 | Chen | |
| 5,033,094 A | 7/1991 | Hung | |
| 5,035,005 A | 7/1991 | Hung | |
| 5,038,412 A | 8/1991 | Cionni | |
| 5,046,192 A | 9/1991 | Ryder | |
| 5,052,194 A | 10/1991 | Jarus | |
| 5,056,161 A | 10/1991 | Breen | |
| 5,086,789 A | 2/1992 | Tichy | |
| 5,095,382 A | 3/1992 | Abe | |
| 5,113,428 A | 5/1992 | Fitzgerald | |
| 5,117,464 A | 5/1992 | Jones et al. | |
| 5,117,465 A | 5/1992 | MacDonald | |
| 5,164,987 A | 11/1992 | Raven | |
| 5,201,856 A | 4/1993 | Edwards | |
| 5,257,420 A | 11/1993 | Byrne, Jr. | |
| 5,265,165 A | 11/1993 | Rauch | |
| 5,285,530 A | 2/1994 | Nardone, Jr. | |
| 5,293,647 A | 3/1994 | Mirmilshteyn et al. | |
| D346,380 S | 4/1994 | Fitzgerald | |
| 5,303,426 A | 4/1994 | Jones | |
| 5,327,178 A | 7/1994 | McManigal | |
| 5,339,467 A | 8/1994 | Brinkley | |
| 5,357,585 A | 10/1994 | Kumar | |
| 5,410,735 A | 4/1995 | Borchardt et al. | |
| 5,509,146 A | 4/1996 | Bryerton, Sr. | |
| 5,528,774 A | 6/1996 | Sanders | |

(56) References Cited

U.S. PATENT DOCUMENTS

| | | | |
|---|---|---|---|
| 5,545,859 A | 8/1996 | Ullrich | |
| 5,551,089 A | 9/1996 | Whidden | |
| 5,551,090 A | 9/1996 | Thompson | |
| D375,825 S | 11/1996 | Whidden | |
| 5,617,589 A | 4/1997 | Lacore et al. | |
| 5,625,903 A | 5/1997 | Schultz et al. | |
| 5,673,438 A | 10/1997 | Lambert | |
| 5,691,515 A | 11/1997 | Landis | |
| 5,708,725 A | 1/1998 | Ito | |
| D390,564 S | 2/1998 | Savona | |
| 5,718,001 A | 2/1998 | Wright | |
| 5,721,775 A | 2/1998 | Leifer | |
| 5,724,119 A | 3/1998 | Leight | |
| 5,749,099 A | 5/1998 | Voorhees | |
| 5,793,878 A | 8/1998 | Chang | |
| 5,821,468 A | 10/1998 | Urella et al. | |
| 5,835,609 A | 11/1998 | LeGette et al. | |
| 5,860,166 A | 1/1999 | Ritts | |
| 5,881,390 A | 3/1999 | Young | |
| 5,887,286 A | 3/1999 | Waldron | |
| 5,898,945 A * | 5/1999 | Weiser | 2/209 |
| 5,943,703 A | 8/1999 | Avila, Jr. | |
| 5,951,141 A | 9/1999 | Bradley | |
| 5,953,434 A | 9/1999 | Boyden | |
| 6,016,574 A | 1/2000 | Chen | |
| 6,029,282 A | 2/2000 | Buschman | |
| 6,055,672 A | 5/2000 | Natvig | |
| 6,065,157 A | 5/2000 | Felman | |
| 6,095,146 A | 8/2000 | Knauer et al. | |
| 6,104,824 A | 8/2000 | Ito | |
| 6,131,204 A | 10/2000 | Otey | |
| 6,148,446 A | 11/2000 | Leight | |
| 6,212,282 B1 | 4/2001 | Mershon | |
| 6,237,157 B1 | 5/2001 | Lobbins | |
| 6,332,223 B1 * | 12/2001 | Le Gette et al. | 2/209 |
| 6,369,958 B1 | 4/2002 | Himmele | |
| 6,377,697 B1 | 4/2002 | Cheng | |
| 6,392,196 B1 | 5/2002 | Lin | |
| 6,406,811 B1 | 6/2002 | Hall et al. | |
| 6,499,146 B2 | 12/2002 | Bavetta et al. | |
| 6,502,247 B2 | 1/2003 | LeGette et al. | |
| 6,502,248 B2 * | 1/2003 | LeGette et al. | 2/209 |
| D473,539 S | 4/2003 | O'Leary | |
| 6,580,800 B1 | 6/2003 | Yamasaki et al. | |
| 6,678,897 B2 | 1/2004 | Lindgren | |
| 6,735,784 B2 | 5/2004 | Isom et al. | |
| 6,744,901 B2 | 6/2004 | Ito et al. | |
| 6,873,862 B2 | 3/2005 | Reshefsky | |
| 6,880,174 B2 | 4/2005 | Prokop | |
| 6,888,950 B2 * | 5/2005 | Siskin et al. | 381/378 |
| 6,918,678 B2 | 7/2005 | McClanahan | |
| 6,920,645 B2 | 7/2005 | LeGette et al. | |
| 6,965,681 B2 | 11/2005 | Almqvist | |
| 6,978,483 B2 | 12/2005 | Isom et al. | |
| 6,980,165 B2 | 12/2005 | Yuasa et al. | |
| 7,020,902 B1 | 4/2006 | Tyler | |
| 7,024,013 B1 | 4/2006 | Van Dam | |
| 7,072,483 B2 | 7/2006 | Lenhard-Backhaus | |
| 7,114,823 B2 | 10/2006 | McCullough et al. | |
| 7,165,272 B2 | 1/2007 | Hudson et al. | |
| D541,482 S | 4/2007 | LeGette et al. | |
| 7,210,173 B2 | 5/2007 | Bavetta et | |
| 7,222,373 B2 | 5/2007 | Healy et al. | |
| D545,001 S | 6/2007 | LeGette et al. | |
| 7,318,654 B2 | 1/2008 | McClanahan | |
| 7,377,666 B1 | 5/2008 | Tyler | |
| 7,424,125 B2 | 9/2008 | Amae et al. | |
| 7,548,617 B2 | 6/2009 | Yuen | |
| 2001/0017925 A1 | 8/2001 | Ceravolo | |
| 2002/0172390 A1 | 11/2002 | Roberts | |
| 2003/0037366 A1 | 2/2003 | Lindgren | |
| 2004/0252487 A1 | 12/2004 | McCullough et al. | |
| 2005/0028250 A1 | 2/2005 | Zaic | |
| 2005/0034216 A1 | 2/2005 | LeGette et al. | |
| 2005/0034218 A1 | 2/2005 | LeGette et al. | |
| 2005/0036643 A1 | 2/2005 | LeGette et al. | |
| 2005/0100184 A1 | 5/2005 | Siskin et al. | |
| 2005/0246815 A1 | 11/2005 | LeGette et al. | |
| 2005/0283882 A1 | 12/2005 | Berger et al. | |
| 2006/0000006 A1 | 1/2006 | Gellis et al. | |
| 2006/0206983 A1 | 9/2006 | Isom et al. | |
| 2007/0107110 A1 | 5/2007 | LeGette et al. | |
| 2007/0154029 A1 | 7/2007 | Werner | |
| 2007/0160249 A1 | 7/2007 | LeGette et al. | |
| 2007/0199133 A1 | 8/2007 | Bavetta et al. | |
| 2007/0220657 A1 | 9/2007 | LeGette et al. | |
| 2007/0226876 A1 | 10/2007 | Foust et al. | |
| 2008/0044052 A1 | 2/2008 | Whipple | |
| 2008/0141439 A1 | 6/2008 | Healy et al. | |
| 2008/0181429 A1 | 7/2008 | Fried | |
| 2008/0216214 A1 | 9/2008 | Dolby | |
| 2008/0279403 A1 | 11/2008 | Pedersen et al. | |
| 2008/0307562 A1 | 12/2008 | Tipp | |
| 2008/0307563 A1 | 12/2008 | LeGette et al. | |
| 2008/0307564 A1 | 12/2008 | LeGette et al. | |
| 2009/0013447 A1 | 1/2009 | Drosihn | |
| 2009/0013448 A1 | 1/2009 | Drosihn | |
| 2009/0154740 A1 | 6/2009 | Regen et al. | |
| 2009/0196453 A1 | 8/2009 | Amae et al. | |
| 2009/0205110 A1 | 8/2009 | Chiang | |
| 2010/0175165 A1 | 7/2010 | Le Gette | |

FOREIGN PATENT DOCUMENTS

| | | |
|---|---|---|
| CH | 662052 | 9/1987 |
| CN | 2291138 | 9/1998 |
| CN | 2353337 Y | 12/1999 |
| DE | 483279 | 9/1929 |
| DE | 641554 | 2/1937 |
| DE | 2516709 A1 | 10/1976 |
| DE | 3231218 A1 | 2/1984 |
| DE | 4422767 A1 | 1/1996 |
| DE | 29800973 U1 | 4/1998 |
| DE | 29812652 U1 | 3/1999 |
| DE | 20003363 U1 | 8/2000 |
| EP | 126690 A1 | 11/1984 |
| EP | 0745364 | 8/2002 |
| FR | 1353524 | 1/1963 |
| FR | 2536253 A1 | 11/1982 |
| FR | 2538204 A1 | 12/1982 |
| FR | 2532838 A1 | 9/1983 |
| GB | 1327614 | 8/1973 |
| GB | 2059206 A | 4/1981 |
| GB | 2062478 | 5/1981 |
| GB | 2226931 A | 7/1990 |
| GB | 2290696 A | 1/1996 |
| GB | 2320885 | 8/1998 |
| GB | 2339642 | 2/2000 |
| JP | 47-19024 | 11/1972 |
| JP | 48-75626 | 9/1973 |
| JP | 53143627 | 11/1978 |
| JP | 54-168912 | 11/1979 |
| JP | 56-152479 | 4/1981 |
| JP | 56-146719 U | 11/1981 |
| JP | 56-164218 U | 12/1981 |
| JP | 5711884 | 1/1982 |
| JP | 6029141 | 2/1982 |
| JP | 57205216 | 12/1982 |
| JP | 5815618 | 1/1983 |
| JP | 58-37289 U | 3/1983 |
| JP | 58-54191 U | 4/1983 |
| JP | 58-104076 | 7/1983 |
| JP | 58138484 | 9/1983 |
| JP | 58-182594 U | 12/1983 |
| JP | 59129815 | 8/1984 |
| JP | 60244188 | 12/1985 |
| JP | 61-42186 | 3/1986 |
| JP | 623526 | 1/1987 |
| JP | 6221016 | 2/1987 |
| JP | 6320232 | 6/1988 |
| JP | 1068506 A | 3/1989 |
| JP | 1068508 A | 3/1989 |
| JP | 1-125320 U | 8/1989 |
| JP | 1125319 | 8/1989 |

(56) References Cited

FOREIGN PATENT DOCUMENTS

| | | |
|---|---|---|
| JP | 05-207581 | 8/1993 |
| JP | 641720 | 6/1994 |
| JP | 6351090 | 12/1994 |
| JP | 1079994 | 3/1998 |
| JP | 1085251 | 7/1998 |
| JP | 3053142 U | 8/1998 |
| JP | 11-229223 | 8/1999 |
| JP | 10257581 | 8/2000 |
| JP | 3082758 | 12/2001 |
| JP | 200211036 | 1/2002 |
| KR | 200226271 | 3/2001 |
| KR | 200314976 | 6/2003 |
| KR | 300336877 | 11/2003 |
| KR | 20357405 | 7/2004 |
| KR | 20357406 | 7/2004 |
| KR | 10-0703878 | 4/2007 |
| SE | 452237 B | 11/1987 |
| WO | 9217079 A1 | 10/1992 |
| WO | 94/02043 A1 | 2/1994 |
| WO | 9409734 A1 | 5/1994 |
| WO | 9748296 A1 | 12/1997 |
| WO | 9807062 A1 | 2/1998 |
| WO | 9831314 A1 | 7/1998 |
| WO | 0176402 A1 | 10/2001 |
| WO | 02083044 A1 | 10/2002 |
| WO | 03086124 A1 | 10/2003 |
| WO | 2005020626 A3 | 3/2005 |
| WO | 2010/017359 A1 | 2/2010 |

OTHER PUBLICATIONS 1999-2000 Catalog "Accessory Goods"—Nitty Company, Ltd. 4 pgs.

Chicago Tribune article entitled "Winter From Head to Toe Lend an Ear to the Tale of This Intrepid Inventor," by Sid Moody, Feb. 16, 1988, 4 pgs.

"History of the United States Patent Office—The Patent Office Pony—A History of the Early Patent Office," by Kenneth W. Dobyns, 1994, [Introductory Material—3 pgs; Chapter 29—4 pgs; and Sources and Annotations—40 pgs.].

2003 Catalog, "Join the Polar Fusion Revolution; Revolutionary Ear Warmers," Polar Fusion LLC.—2 pgs.

Nitty Company Ltd. Winter '89-'90 catalog, 6 pages.

Nitty Company Ltd., Winter '90-'91 catalog, 4 pages.

"Hearmuff: Fleece headwear with internal stereo headphones" from http://www.hearmuff.com/index.htm, 2003, 1 pg.

"Hearmuffs" from http://www.hearmuff.com/goods.htm, 2003, 2 pgs.

"Hearmuffs" from http://www.hearmuff.com/about.htm, 2003, 3 pgs.

Opinion from the District Court of Maryland in 180s, Inc. and 180s, LLC v. Gordini U.S.A., Inc. (Case 1:08-cv-00177-JFM), 23 pages, dated Mar. 30, 2010.

Defendant Gordini's First Supplemental and Amended Answers and Objections to Plaintiffs Second Set of Interrogatories (Non-Confidential Version) from 180s, Inc. and 180s, LLC v. Gordini U.S.A., Inc. (Case 1:08-cv-00177-JFM), 29 pages, dated Feb. 4, 2009.

\* cited by examiner

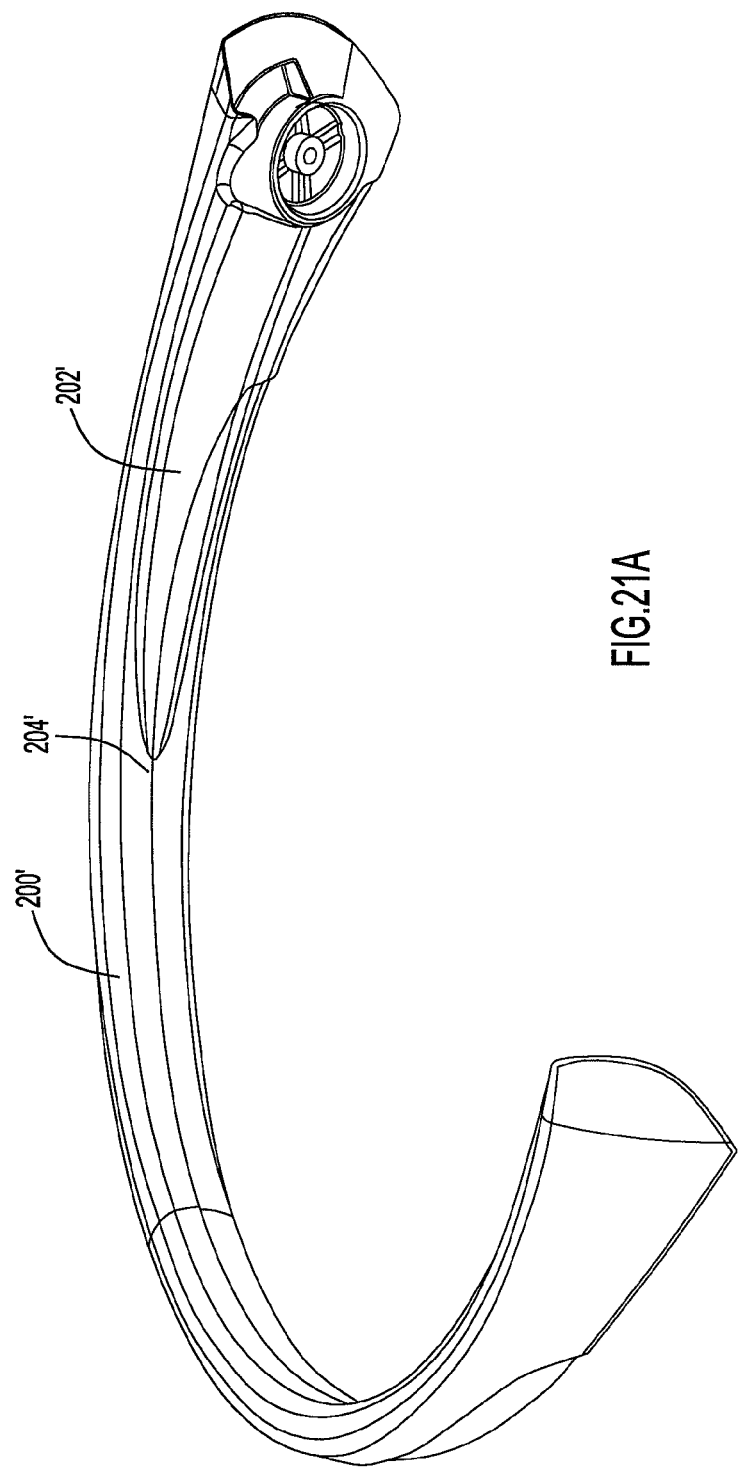

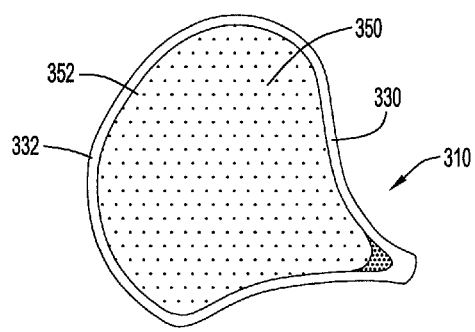
FIG.26
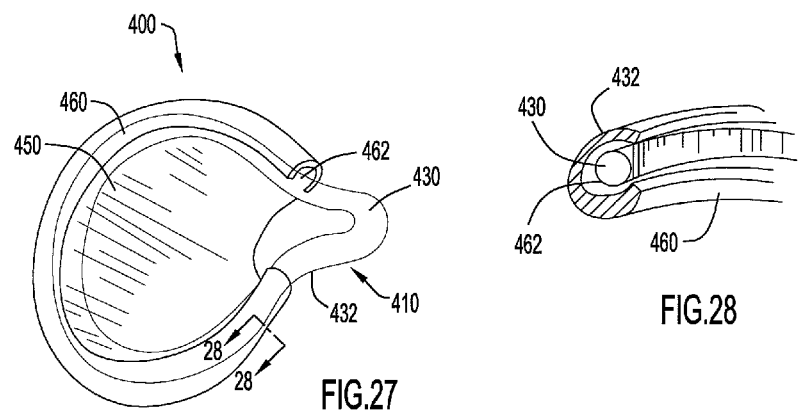
FIG.27
FIG.28

EAR WARMER WITH FABRIC MEMBER

CROSS-REFERENCES TO OTHER APPLICATIONS

This application is a divisional application of U.S. patent application Ser. No. 10/638,476, entitled "Ear Warmer Having an External Frame," filed Aug. 12, 2003, now U.S. Pat. No. 7,650,649, the disclosure of which is incorporated by reference herein in its entirety. This application is related to U.S. patent application Ser. No. 12/168,015, entitled "Ear Warmer with a Substantially Continuous Surface," filed Jul. 3, 2008, published as U.S. patent application Pub. No. 2008/0307564, and to U.S. patent application Ser. No. 12/168,001, entitled "Ear Warmer With Fabric Member," filed Jul. 3, 2008, published as U.S. patent application Pub. No. 2008/0307563, the disclosure of each of which is incorporated by reference in its entirety. This application is also related to U.S. patent application Ser. No. 10/693,607, entitled "Ear Warmer having a Curved Ear Portion," filed Oct. 27, 2003, now U.S. Pat. No. 7,962,970, the disclosure of which is incorporated by reference in its entirety. This application is also related to U.S. patent application Ser. No. 11/754,327, filed May 28, 2007, entitled "Ear Warmer Having a Membrane Forming a Receptacle," published as U.S. patent application Pub. No. 2008/0141439, which is a continuation of U.S. patent application Ser. No. 10/638,554, entitled "Ear Warmer Having a Membrane Forming a Receptacle," filed Aug. 12, 2003, now U.S. Pat. No. 7,222,373, the disclosure of each of which is incorporated by reference in its entirety. This application is also related to U.S. patent application Ser. No. 11/688,712, filed Mar. 20, 2007, entitled "Ear Warmer With a Speaker System," published as U.S. patent application Pub. No. 2007/0160249, which is a continuation of U.S. patent application Ser. No. 10/638,553, entitled "Ear Warmer With a Speaker System," filed Aug. 12, 2003, now U.S. Pat. No. 7,212,645, the disclosure of each of which is incorporated by reference in its entirety.

BACKGROUND OF THE INVENTION

This invention relates generally to ear warmers, and in particular to ear warmers that have a frame and are configured to extend around a back of a user's head.

Conventional ear warmers extend over a top of a user's head. Such a conventional ear warmer typically has a frame and a layer of fabric on each side of an ear portion of the frame. These layers of fabric and the frame itself typically have a weight appropriate for sedentary outdoor-activities, but not for non-sedentary outdoor-activities such as running or jogging. In other words, when participating in certain outdoor activities, the participant desires apparel that keeps him or her warm while minimizing the weight of such apparel. While capable of keeping the user warm, conventional ear warmers do not have such desired minimal weight.

Thus, a need exists for an ear warmer that is lightweight while still providing warmth to the user.

SUMMARY OF THE INVENTION

An ear warmer comprises a frame and a fabric member. The frame has an ear portion and a band portion. The ear portion of the frame includes a first side and a second side opposite the first side. The first side of the ear portion defines an interior portion of an opening. The second side of the ear portion defines an exterior portion of the opening. The fabric member includes at least its own ear portion coupled to a portion of the frame. In one embodiment, the ear portion of the fabric member covers the interior portion of the opening in substantially its entirety. In one embodiment, the ear portion of the fabric member covers less than an entirety of the exterior portion of the opening.

BRIEF DESCRIPTION OF THE DRAWINGS

FIG. 21A is a perspective view of an alternative embodiment of a band portion of a frame according to an embodiment of the invention.

FIG. 26 is a side view of a portion of an ear warmer according to an embodiment of the invention.

FIGS. 27 and 28 are a side view and cross-section view along line 28-28, respectively, of a portion of an ear warmer having a press-fit connection, according to an embodiment of the invention.

DETAILED DESCRIPTION

An ear warmer comprises a frame and a fabric member. The frame has an ear portion and a band portion. The ear portion of the frame includes a first side and a second side opposite the first side. The first side of the ear portion defines an interior portion of an opening. The second side of the ear portion defines an exterior portion of the opening. The fabric member includes at least its own ear portion coupled to a portion of the frame. In one embodiment, the ear portion of the fabric member covers the interior portion of the opening in substantially its entirety. In one embodiment, the ear portion of the fabric member covers less than an entirety of the exterior portion of the opening. The term "less than an entirety" should be understood to mean that the fabric member covers some of the exterior portion of the opening or none of the exterior portion of the opening.

Figure 1:
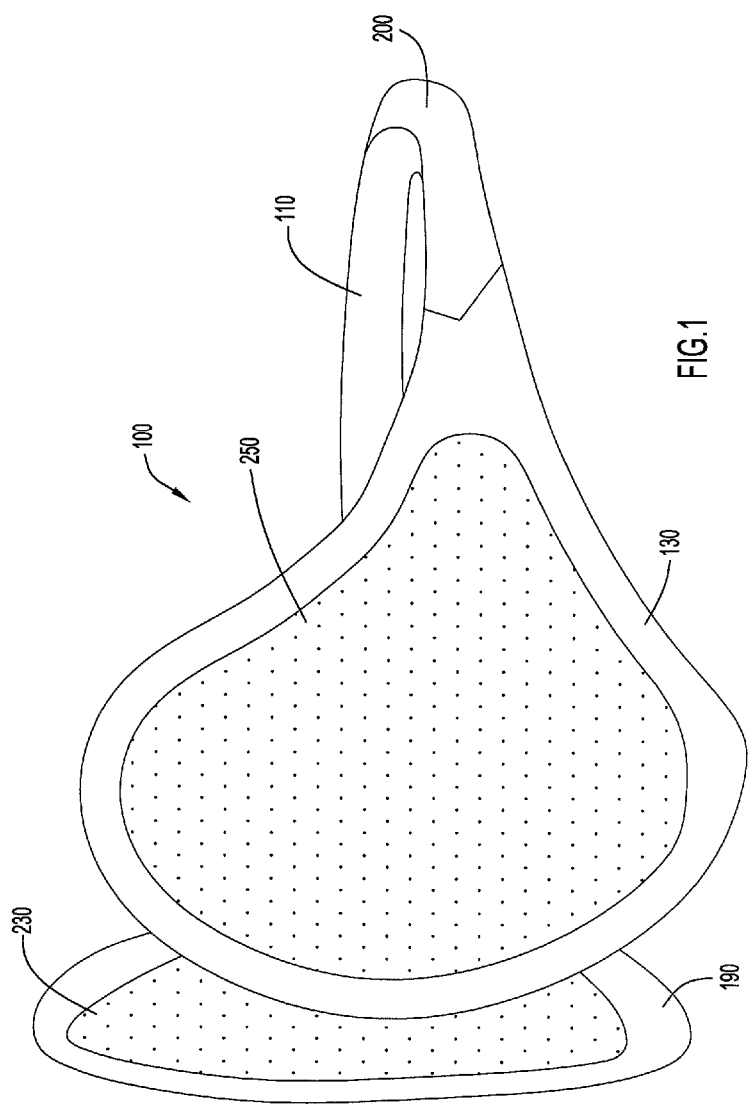
FIG. 1 is a perspective view of an ear warmer in an expanded configuration according to an embodiment of the invention.
Figure 2:
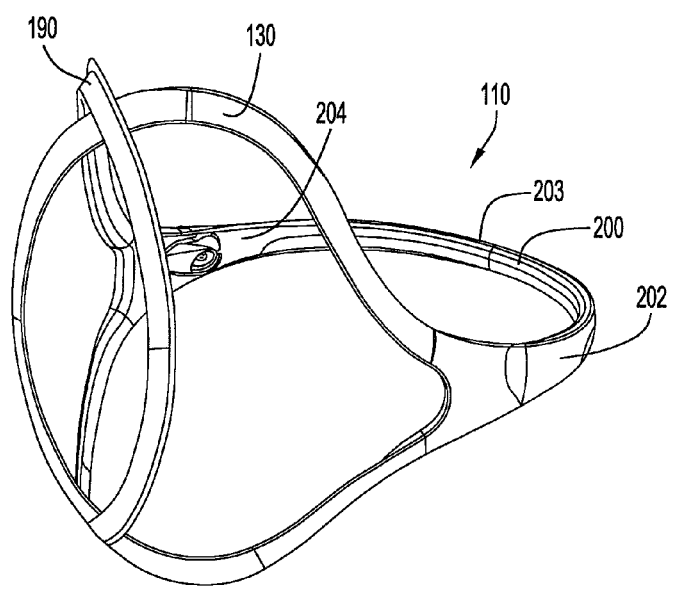
FIG. 2 is a front perspective view of the frame of the ear warmer illustrated in FIG. 1.
Figure 3:
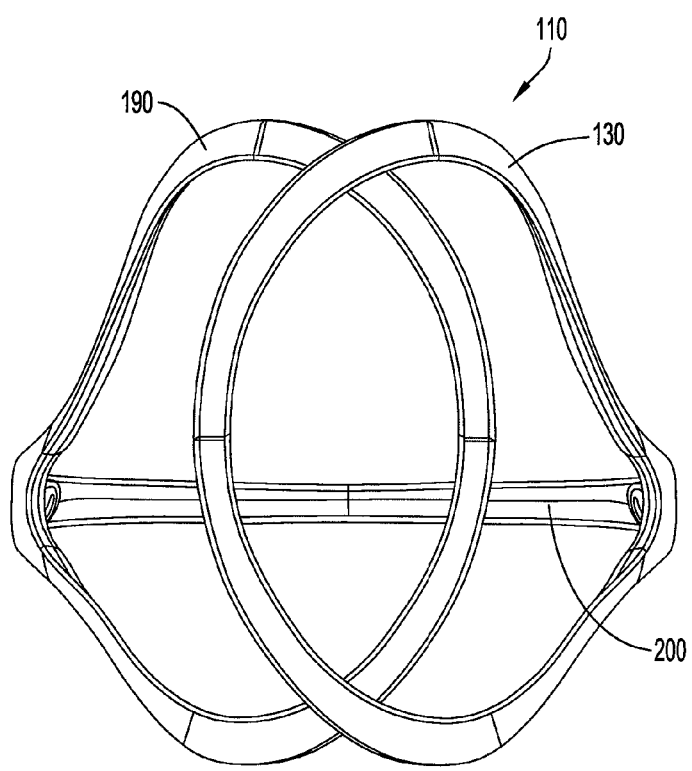
FIG. 3 is a front view of the frame of the ear warmer illustrated in FIG. 2.

An ear warmer 100 according to an embodiment of the invention is illustrated in FIG. 1. In this embodiment, the ear warmer 100 includes a frame 110 and two fabric members 230 and 250. The ear warmer 100 is disposable in an expanded configuration and in a collapsed configuration. The frame 110 of the ear warmer 100 includes a first ear portion 130, a second ear portion 190 and a band portion 200. In this embodiment, fabric member 250 is coupled to the first ear portion 130. Similarly, fabric member 230 is coupled to the second ear portion 190. The fabric members 230 and 250 can be fixedly or removably coupled to the respective ear portions. Various techniques for coupling of the fabric members 230 and 250 are discussed below in detail.

In an alternative embodiment, the frame 110 can be a single piece of material in which the first ear portion 130, the second ear portion 190 and the band portion 200 are formed monolithically (i.e., unitary construction). In another embodiment, the band portion 200 can be adjustable in length. In another embodiment, the first ear portion 130 and the second ear portion 190 can be fixedly coupled to the band portion 200.

Figure 22:
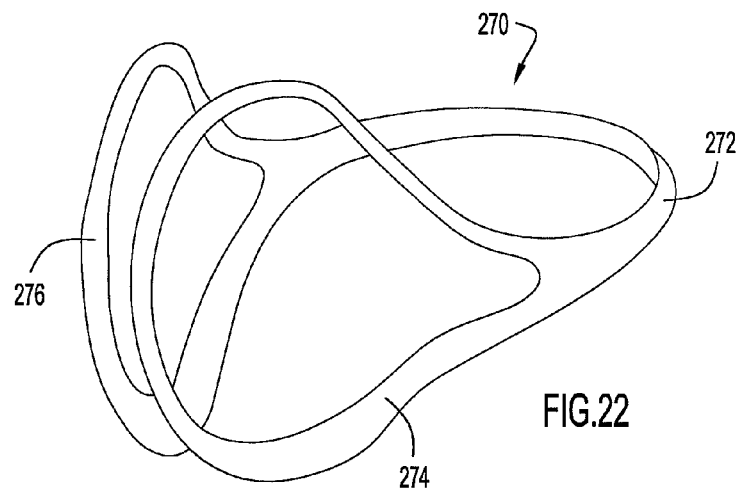
FIGS. 22-23 are perspective views of frames according other embodiments of the invention.

An embodiment of a single-piece frame is illustrated in FIG. 22. In this embodiment, the frame 270 includes a band portion 272, a first ear portion 274 and a second ear portion 276. The first ear portion 274 and the second ear portion 276 are not collapsible with respect to the band portion 272. The frame 270 can have an expanded configuration corresponding to a position on the user's head and an unexpanded configuration corresponding to a position off the user's head. The frame 270 can have an inward bias that defines the unexpanded configuration. Although the user's head is not shown, FIG. 22 shows the frame 270 in the expanded configuration. In alternative embodiments, the position of ear portions 274 and 276 in the expanded and unexpanded configurations can differ from that shown in FIG. 22.

Figure 23:
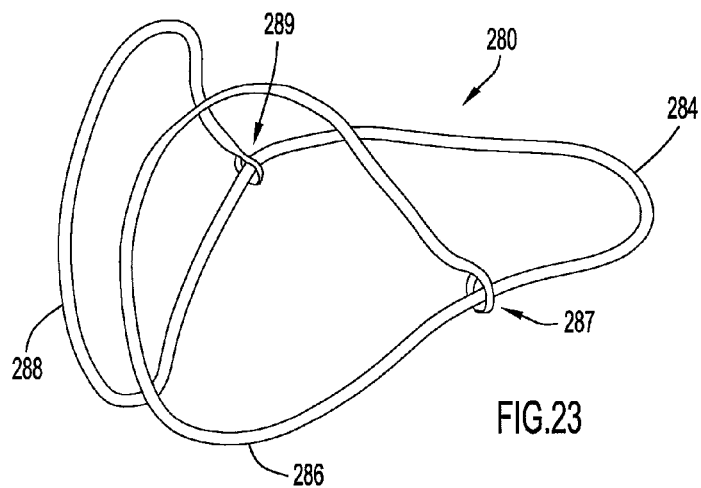

An embodiment of an alternative frame is illustrated in FIG. 23. In this embodiment, the frame 280 has unitary construction including a band portion 284, a first ear portion 286 and a second ear portion 288. The first ear portion 286 has an end portion 287 that couples to the band portion 284. The second ear portion 288 has an end portion 289 that couples to the band portion 284. In this embodiment, the ends 287 and 289 are wrapped around the band portion 284.

Figure 10:
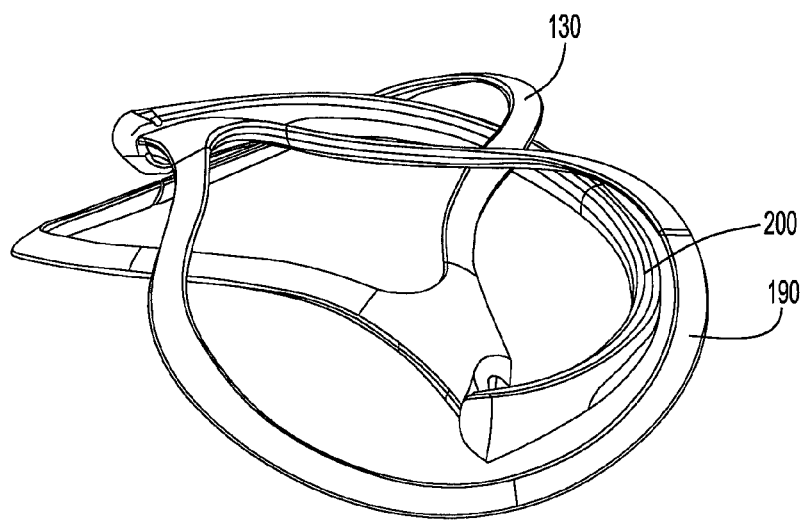
FIG. 10 is a perspective view of the frame of the ear warmer illustrated in FIG. 2 in a collapsed configuration.
Figure 11:
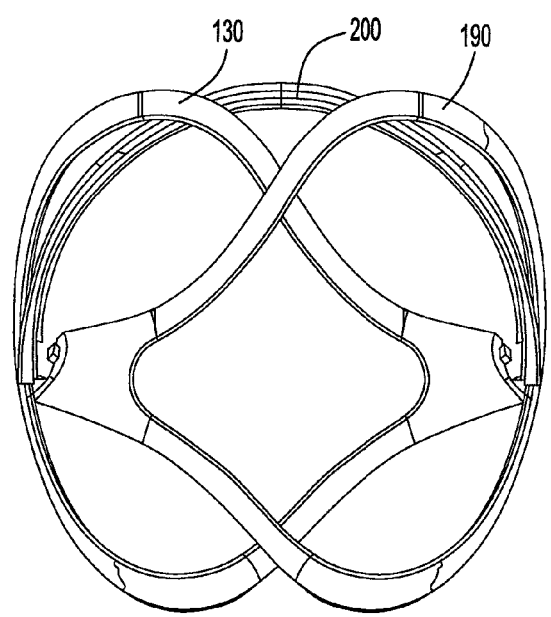
FIG. 11 is a top view of the frame of the ear warmer illustrated in FIG. 2 in a collapsed configuration.
Figure 12:
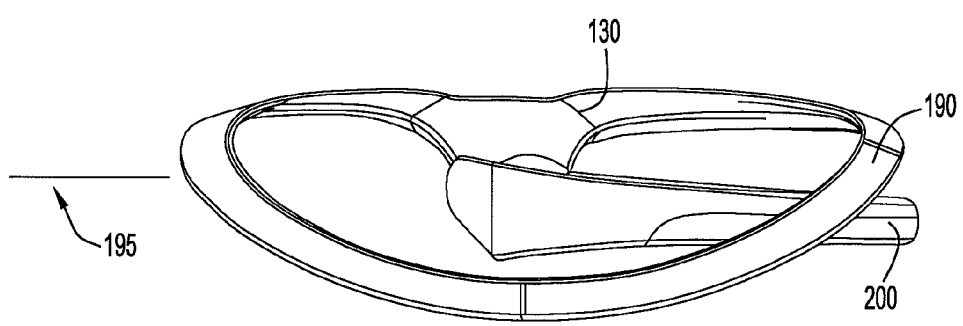
FIG. 12 is a side view of the frame of the ear warmer illustrated in FIG. 2 in a collapsed configuration.

FIGS. 2 through 9 illustrate the frame 110 of the ear warmer 100 in an expanded configuration. FIGS. 10 through 12 illustrate the frame 110 of the ear warmer 100 in a collapsed configuration. The frame 110 includes a band portion 200, a first ear portion 130 coupled to the band portion 200, and a second ear portion 190 coupled to the band portion 200.

As illustrated in FIGS. 2 through 9 and 17 through 21, the band portion 200 is configured to extend around the back of a user's head. The band portion 200 includes a middle portion 203, a first end portion 202, and a second end portion 204. The band portion 200 has an inner side 206 (the side that is disposed adjacent a user when the ear warmer is worn by the user), an outer side 208 (the side opposite the inner side and distal from a user when the ear warmer is worn by the user), an upper side 210 (the side that faces up when the ear warmer is worn by a user), and a lower side 212 (the side that faces down when the ear warmer is worn by a user).

Figure 4:
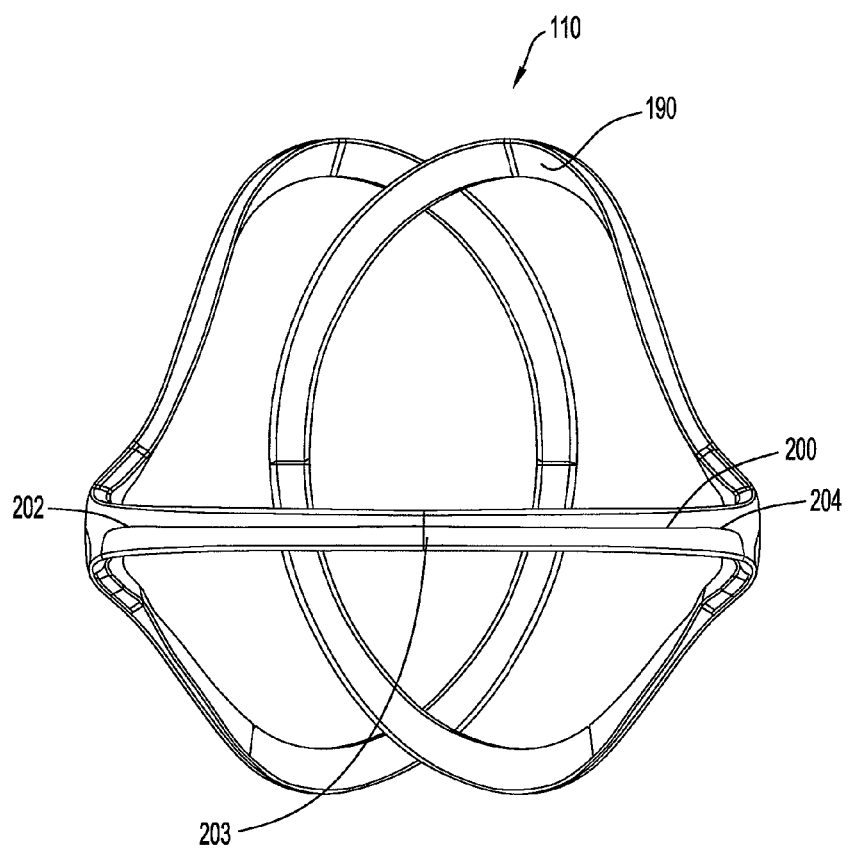
FIG. 4 is a rear view of the frame of the ear warmer illustrated in FIG. 2.
Figure 5:
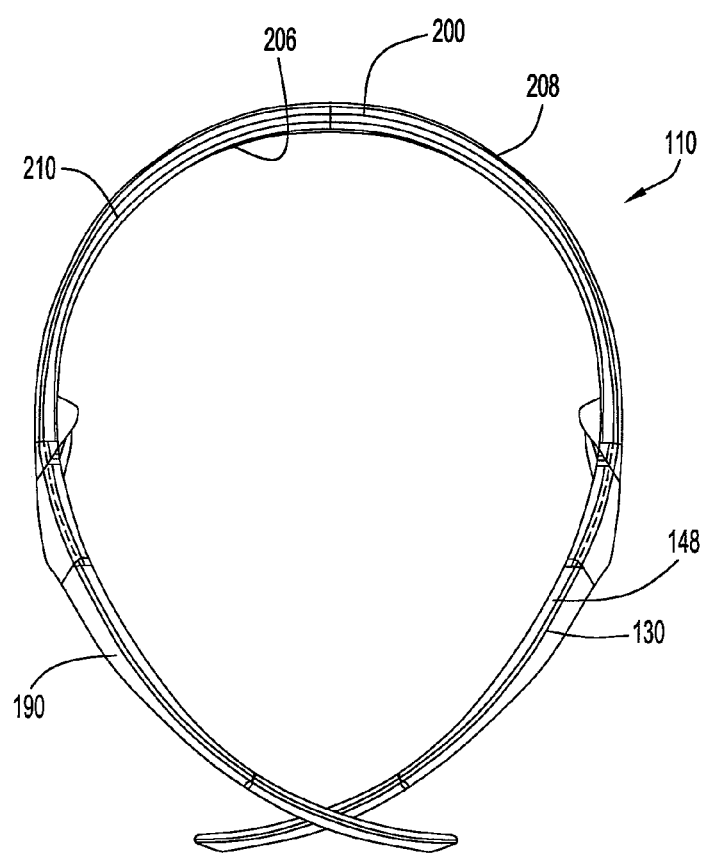
FIG. 5 is a top view of the frame of the ear warmer illustrated in FIG. 2.
Figure 6:
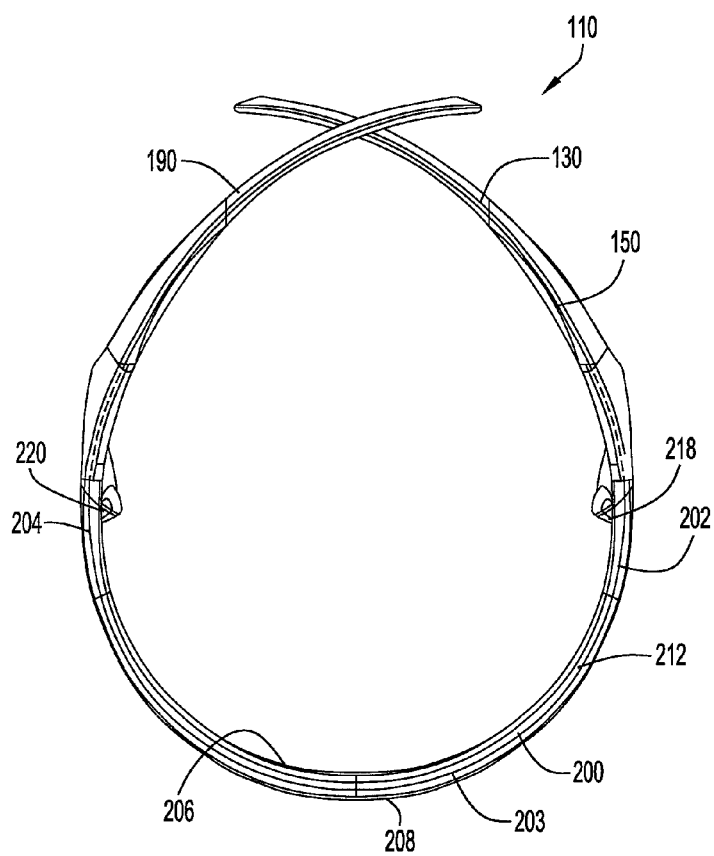
FIG. 6 is a bottom view of the frame of the ear warmer illustrated in FIG. 2.
Figure 7:
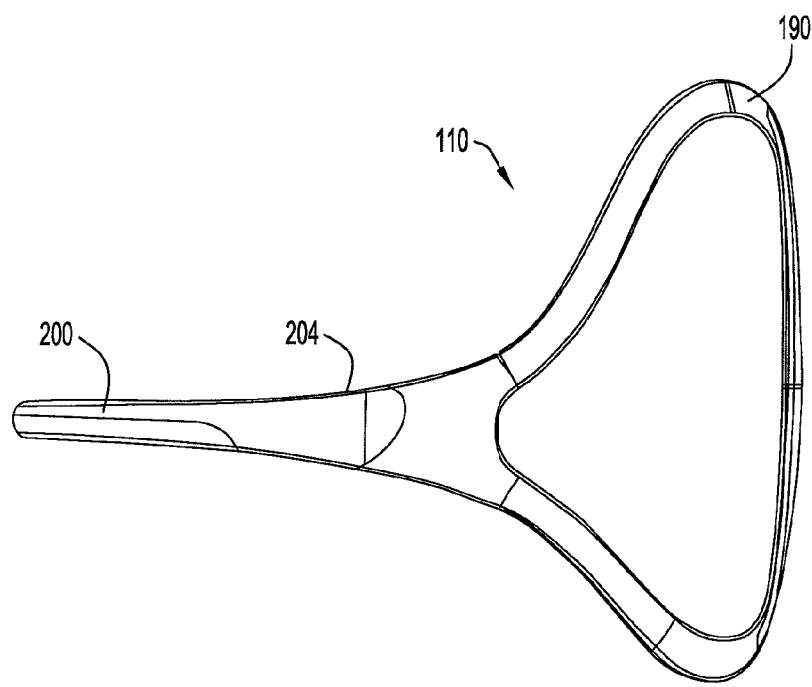
FIG. 7 is a right side view of the frame of the ear warmer illustrated in FIG. 2.
Figure 8:
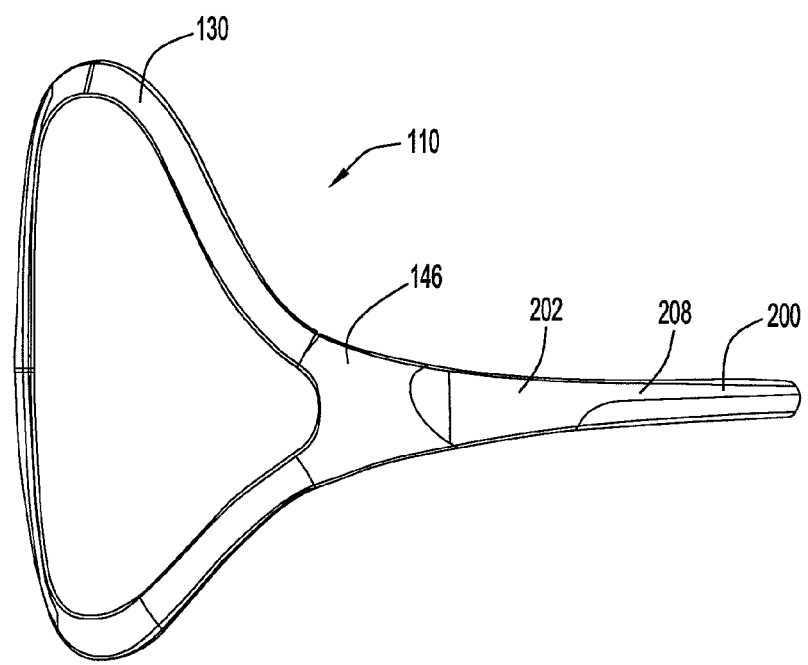
FIG. 8 is left side view of the frame of the ear warmer illustrated in FIG. 2.
Figure 9:
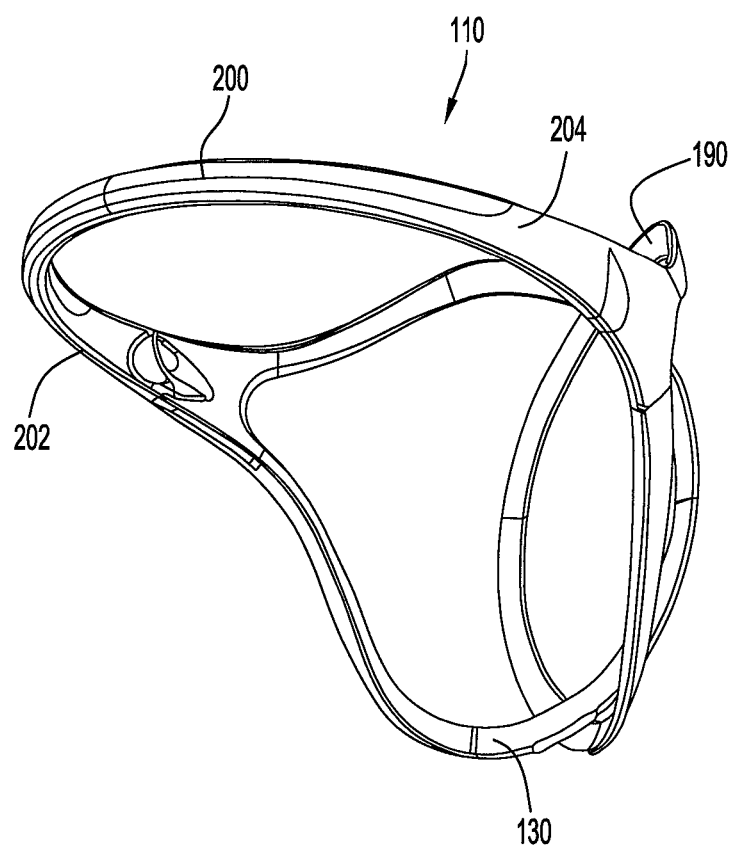
FIG. 9 is a rear perspective view of the frame of the ear warmer illustrated in FIG. 2.

In one embodiment the band portion 200 varies in a height dimension and has a substantially tapered shape (see FIG. 4). As illustrated in FIG. 4, the middle portion 203 of the band portion 200 is of a lesser height or thickness than either of the first end portion 202 of the band portion 200 and the second end portion 204 of the band portion 200. In an alternative embodiment, the band portion 200 has a constant height or thickness.

Referring to FIGS. 17-21, the first end portion 202 of the band portion 200 includes a first coupling portion 218 configured to be coupled to the first ear portion 130 of the frame 110. Similarly, the second end portion 204 of the band portion 200 includes a second coupling portion 220 configured to be coupled to the second ear portion 190 of the frame 110. In this embodiment, the first coupling portion 218 and the second coupling portion 220 are substantially similar in function and structure with the exception that they are reverse images of each other. Therefore, only the first coupling portion 218 of the band member 200 will be discussed in detail. In alternative embodiments, the coupling portions may have different configurations and/or structures.

Figure 17:
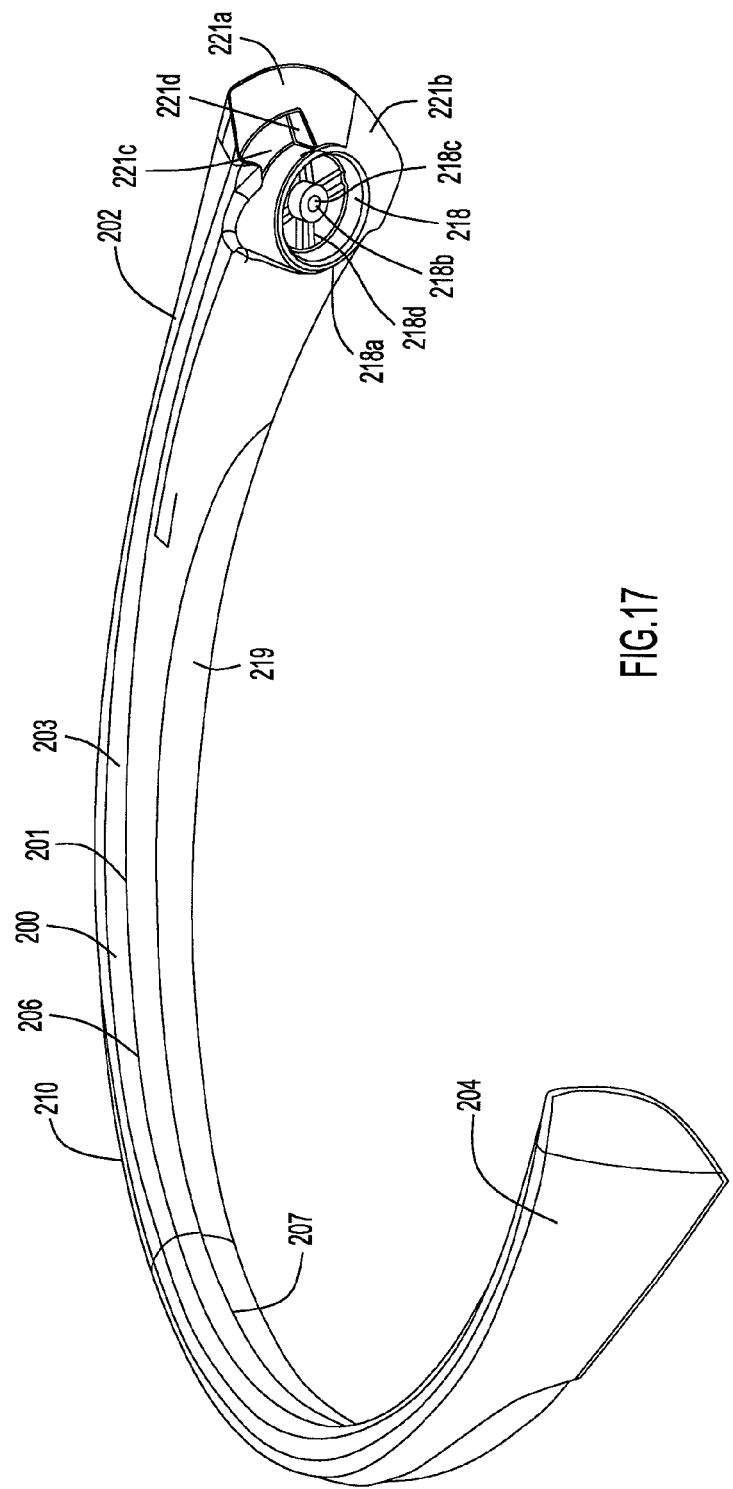
FIG. 17 is a perspective view of a band portion of the frame of the ear warmer illustrated in FIG. 2.
Figure 18:
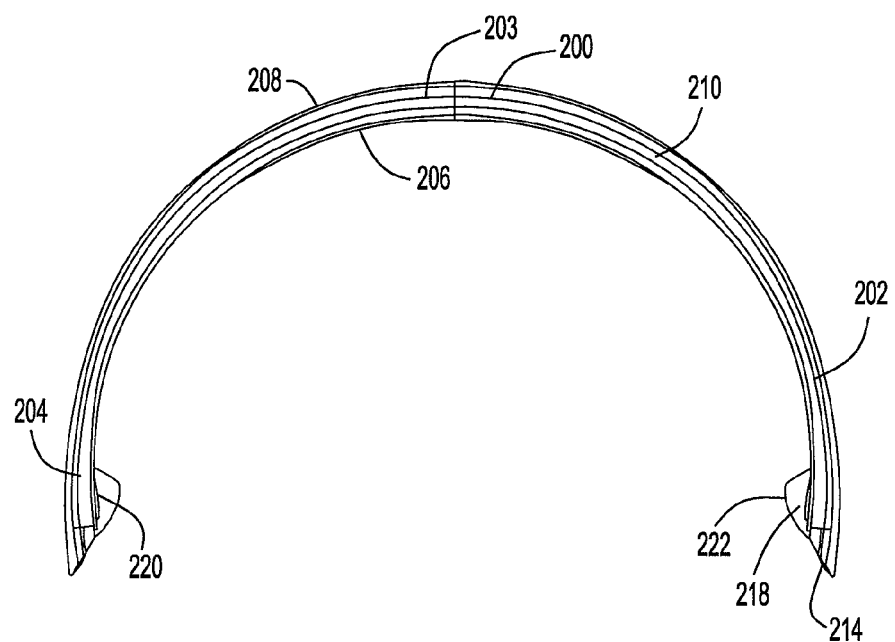
FIG. 18 is a top view of the band portion illustrated in FIG. 17.

As illustrated in FIGS. 17 and 18, the first coupling portion 218 includes an end surface 214 of the band portion 200 and includes distal end 222. The distal end 222 of the first coupling portion 218 has a mounting structure and defines a planar surface (also referred to herein as the "oblique plane"). Although in one embodiment the mounting structure is cylindrical in shape, the mounting structure need not be cylindrical in shape. The coupling portion and mounting structure may be of any shape, such as cubic or rectangular.

Figure 19:
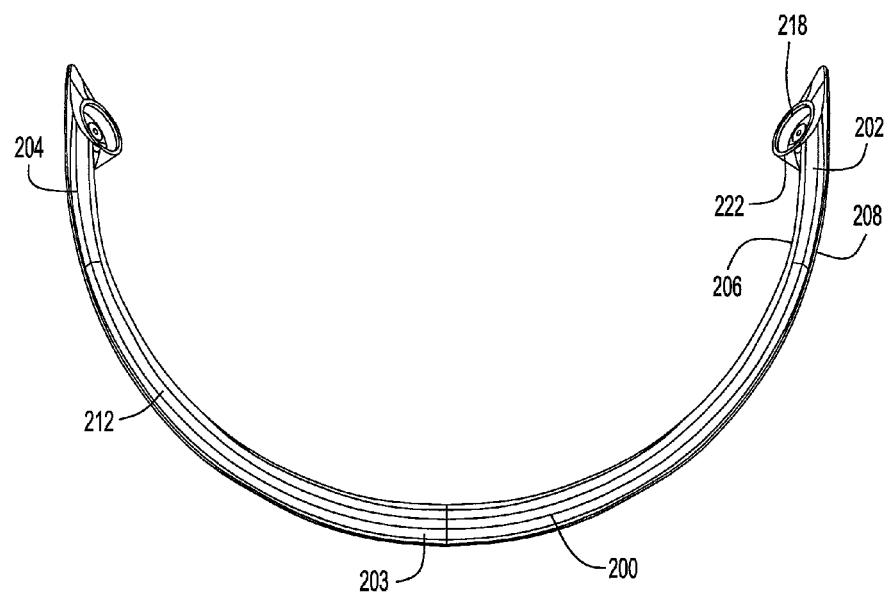
FIG. 19 is a bottom view of the band portion illustrated in FIG. 17.
Figure 20:
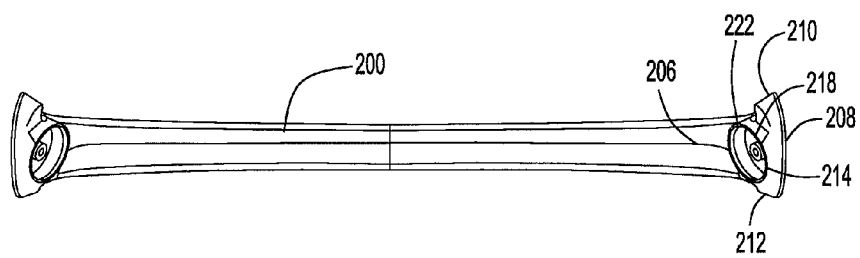
FIG. 20 is a front view of the band portion illustrated in FIG. 17.

Referring to FIG. 20, the oblique plane is oblique to the surfaces defined by the upper side 210 and lower side 212 of the band portion 200. Additionally, as illustrated in FIG. 19, the oblique plane is oblique to the surfaces defined by the inner side 206 proximate the coupling portion 218 and the outer side 208 of the band portion 200 proximate the coupling portion 218.

In one embodiment, the oblique plane enables the ear portion to move upwardly and inwardly to a collapsed configuration as described below. In an alternative embodiment, the end surface of the band portion is at an oblique plane with respect to only one side of the band portion. Alternatively, the end surface of the band portion can be substantially perpendicular to the outer surface of the band portion.

In one embodiment, the frame, including the band portion and the ear portions, is made of a single material. In another embodiment, the frame is made of polypropylene. In alternative embodiments, the frame is made of a thermoplastic resin material, such as Crastin® sold by DuPont, or Grillamid®.

In an alternative embodiment, the band portion 200 includes a recess 207 (see FIG. 17). In this embodiment, the band portion 200 is made of a first material 201 and a second material 219 (see FIG. 17). The second material 219 may be any material that increases friction contact. Also, the second material 219 can be any material that can distribute the force of the ear warmer 100 when retained on the user. In the embodiment shown in FIG. 17, the second material extends for less than the entire height of the band portion. In alternative embodiments, the second material can be on the inside of the band portion only, the inside and outside of the band portion, or the outside of the band portion only. Alternatively, the second material can be disposed in two or more separate locations on the band portion. In an alternative embodiment, the second material extends across an entire width of the band portion. In one embodiment, the first material 201 is a plastic material and the second material 219 is a rubber material. Although the band portion of the frame is illustrated as being elongated, the band portion need not be elongated in shape.

Referring to FIG. 17, the coupling portion 218 is illustrated and described in detail. In this embodiment, the coupling portions 218 and 220 are substantially the same. Accordingly, only coupling portion 218 is described in detail. It is to be understood that alternative embodiments of the band portion to not necessarily need to have all of the features and/or structures discussed with respect to coupling portion 218. In other words, alternative coupling portions can have any combination of the structures.

Referring to FIG. 17, the coupling portion 218 includes a mounting structure 218a that in substantially cylindrical in shape. The mounting structure 218a has a lower surface that can include one or more recesses or notches 218d, the function of which is described later. The mounting structure 218a also includes a center shoulder 218b that has an opening 218c that is configured to receive a connector, such as a screw.

In one embodiment, the end of the band portion 200 includes a first end surface 221a and a second end surface 221b that is proximate to surface 221a. The surfaces 221a and 221b are offset and at an angle with respect to each other. The configuration of surfaces 221a and 221b assist with the movement of the ear portion with respect to the band portion. In an alternative embodiment, surfaces 221a and 221b are disposed in the same plane. As described below, surfaces 221a and 221b form contact surfaces that limit the rotation of the ear portion relative to the band. The end of the band portion 200 also includes another surface 221a and a shoulder 221d adjacent surface 221c. The surface 221c and shoulder 221d form an abutment that is contacted by the ear portion to limit the rotation of the ear portion with respect to the band portion 200. In an alternative embodiment, the band portion does not include a surface and shoulder as previously described.

In one embodiment, the band portion includes a coupler that is configured to removably couple a label, such as a brand label, to the band portion. In one embodiment, the coupler is disposed at the rear of the band portion. In alternative embodiments, the coupler is disposed on a side of the band portion, for example near the portion of the band, which couples to the ear portion, or at any other location on the band portion.

Figure 21:
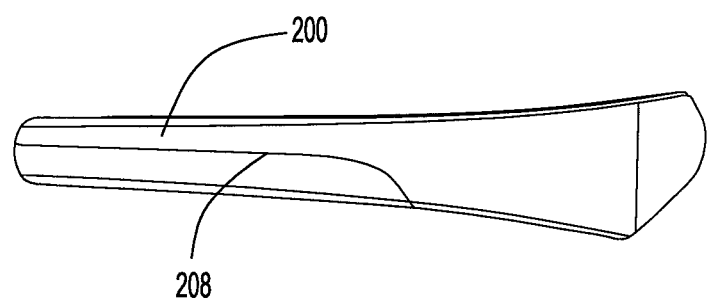
FIG. 21 is a side view of the band portion illustrated in FIG. 17.
Figure 21B:
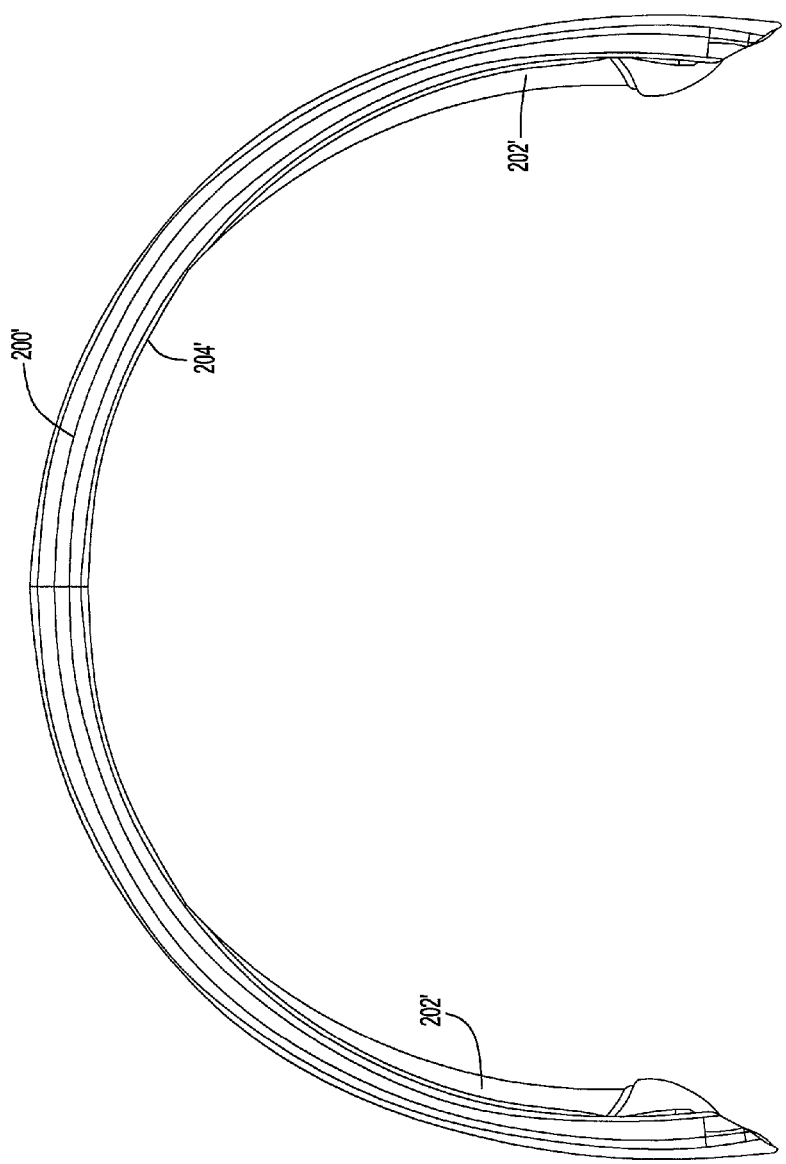
FIG. 21B is a top view of an alternative embodiment of a band portion of a frame according to an embodiment of the invention.

An alternative embodiment of the band portion is illustrated in FIGS. 21A and 21B. In this embodiment, a band portion 200' includes support members 202' disposed on the inner surface 204' of the band portion 200'. Support members 202' are configured to provide added strength and support to the band portion 200'.

An embodiment of an ear portion is illustrated in FIGS. 13-16. In this embodiment, the first ear portion 130 of the frame 110 and the second ear portion 190 of the frame 110 are substantially similar in function and structure. Therefore, only the first ear portion 130 is discussed in detail.

As illustrated in FIGS. 13 through 16, the first ear portion 130 of the frame 110 defines an opening 134 and a center point 152. The first ear portion 130 includes a proximal end portion 156, which includes a proximal end point 136 (the portion and point being proximate to the coupling of the first ear portion 130 and the band portion 200); a distal end portion 158, which includes a distal end point 138 (the portion and point being distal from the coupling of the first end portion 130 and the band portion 200); an uppermost portion 160, which includes an uppermost point 140 (the portion and point being uppermost when the ear warmer is disposed in an expanded configuration on a user); and a lowermost portion 162, which includes a lowermost point 142 (the portion and point being lowermost when the ear warmer is disposed in an expanded configuration on a user).

Although points on the first ear portion 130 have been identified as being proximal, distal, uppermost, and lowermost, it should be understood that there may be, for example, several uppermost points of the first ear portion. In such a case, the "uppermost point" includes the several points. The same is true for the proximal, distal, and lowermost points. In addition, the terms proximal, distal, uppermost, and lowermost are used for convenient reference with respect to the orientation shown in FIGS. 2 through 9 and 13 through 16. It should be understood that these locations of the frame are still applicable regardless of the orientation of the frame at any given time.

Figure 13:
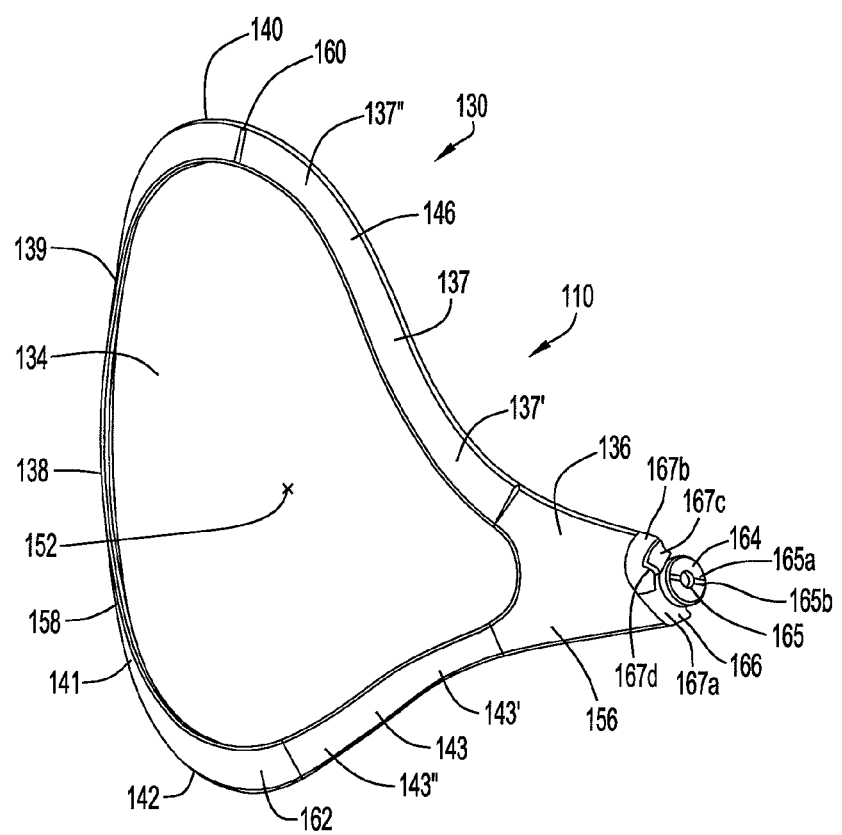
FIG. 13 is a perspective view of an ear portion of the frame of the ear warmer illustrated in FIG. 2.
Figure 15:
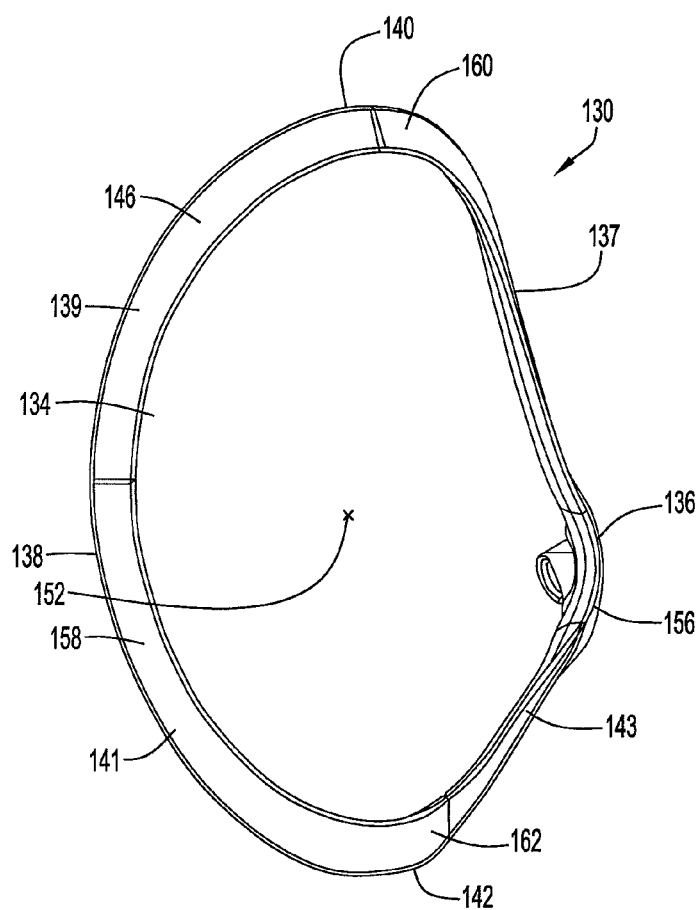
FIG. 15 is a front view of the ear portion illustrated in FIG. 13.
Figure 16:
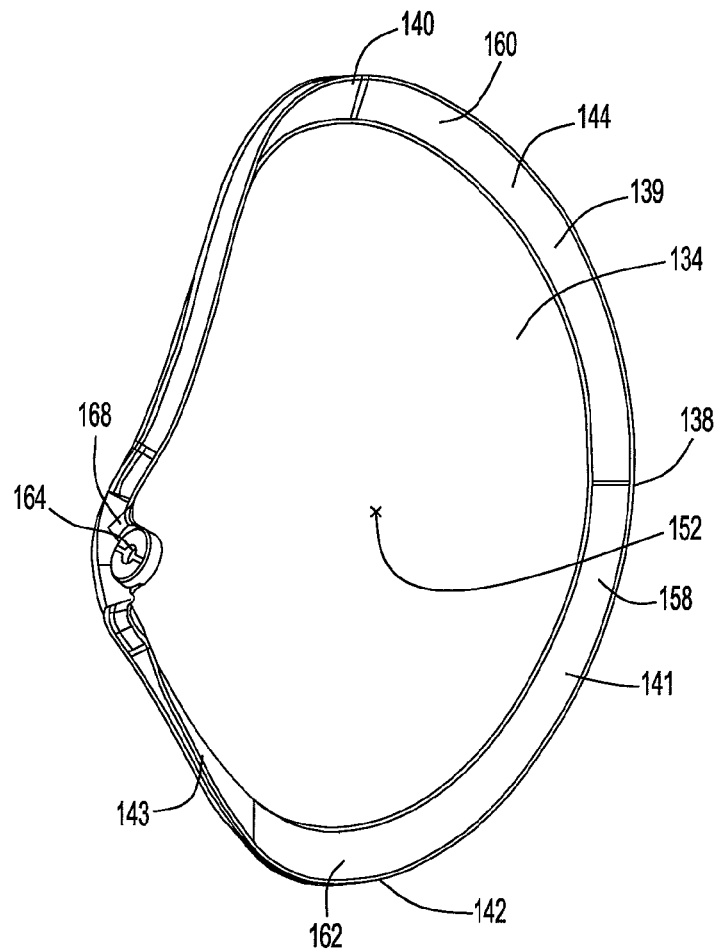
FIG. 16 is a rear view of the ear portion illustrated in FIG. 13.

As illustrated in FIGS. 13 and 15, a portion 137 of the first ear portion 130 of the frame 110 is disposed between the proximal end point 136 and the uppermost point 140 and has a first part 137' and a second part 137". From a side view of the first ear portion 130 (see FIG. 13), the first part 137' of the portion 137 has a convex configuration with respect to the center point 152. Similarly, a portion 143 of the first ear portion 130 of the frame 110 is disposed between the lowermost point 142 and the proximal end point 136. The portion 143 has a first part 143' and a second part 143". From a side view, the first part 143' of the portion 143 has a convex configuration with respect to the center point 152. In other words, at least a portion of each of the portions 137 and 143 of the first ear portion 130 bend or curve away from the center point 152. The location and number of inflection points in portions 137 and 143 can vary along the ear portion.

From a side view of the first ear portion 130, the portion 139 of the first ear portion 130 of the frame 110 that is disposed between the uppermost point 140 and the distal end point 138 has a concave configuration with respect to the center point 152. Similarly, the portion 141 of the first ear portion 130 of the frame 110 that is disposed between the distal end point 138 and the lowermost point 142 has a concave configuration with respect to the center point 152. In other words, at least a portion of each of the portions 139 and 141 of the first ear portion 130 bend toward the center point 152. In alternative embodiments one or both of the portions 139 and 141 can include a concave portion or section and a convex portion or section, relative to the center point.

Figure 14:
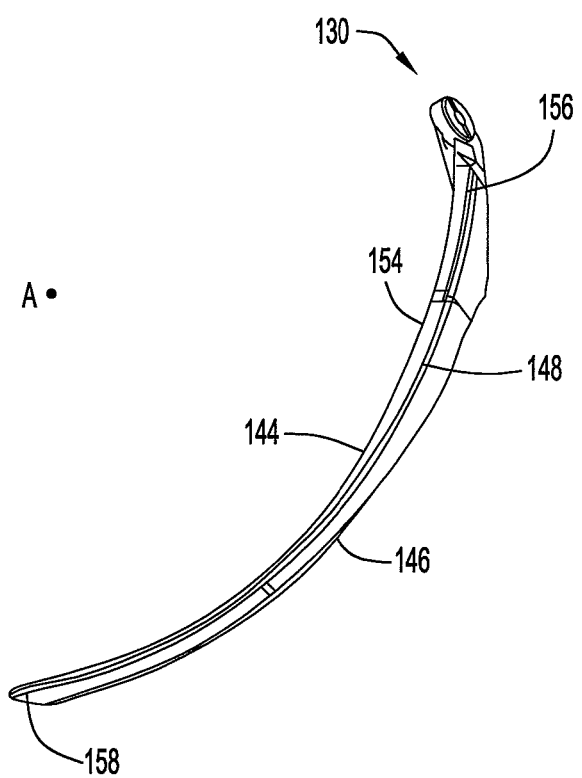
FIG. 14 is a top view of the ear portion illustrated in FIG. 13.

Referring to FIG. 14, the first ear portion 130 includes an inner side 144 (the side that is disposed adjacent a user when the ear warmer is worn by the user), an outer side 146 (the side opposite the inner side and distal from a user when the ear warmer is worn by the user), an upper side 148 (the side that faces up when the ear warmer is worn by a user), and a lower side 150 (see FIG. 13) (the side that faces down when the ear warmer is worn by a user). The inner side 144 of the first ear portion 130 defines an interior portion or region of the opening 134. Similarly, the outer side 146 of the first ear portion 130 defines an exterior portion or region of the opening 134.

As illustrated in FIG. 14, the inner side 144 of the first ear portion 130 of the frame 110 has an innermost surface 154. The innermost surface 154 is the portion of the inner side 144 of the first ear portion 130 directly adjacent a user's head when the ear warmer 100 is worn by the user. Referring to FIG. 14, a top view of a two-dimensional projection of the innermost surface 154 is a curved line that curves around a point A, which is disposed on the inner side of the first ear portion 130. In other words, the first ear portion 130 is curved such the distal end portion 158 is configured to be disposed closer to a user's head, or to place more pressure on the user's head (if the entire portion of the frame is contacting the user's head), than a mid-point of the innermost surface 154 when the ear warmer 100 is worn by the user. This is due to the fact that the curvature of the user's head may be different from the curvature of the ear portion. Said another way, the frame 110 is configured to apply lateral forces to the user's head inwardly where the forces are greatest at the distal end portion 158.

In one embodiment, the distal end portion 158 of the frame 110 is flexible. Thus, the lateral force of the distal end portion 158 against a user's head causes the distal end portion to bend or flex and, thus, to better fit along the user's head. In an alternative embodiment, the first ear portion is curved such that the distal end portion of the first ear portion is configured to be disposed closer to a user's head than the proximal end portion of the first ear portion when the ear warmer is worn by the user. In a further alternative embodiment, the portion of the innermost surface disposed between the proximal end portion and the distal end portion does not have a curved shape.

Figure 14A:
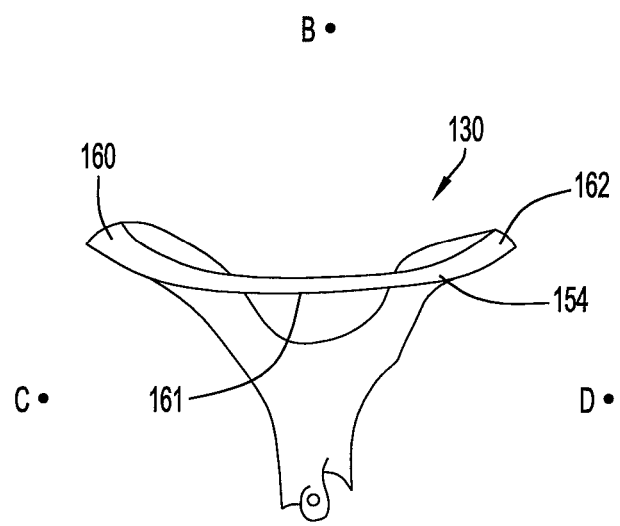
FIG. 14A is a front perspective view of the ear portion illustrated in FIG. 13.

As illustrated in FIG. 14a, a two-dimensional projection of a front view of the innermost surface 154 is a curved line that has three radii of curvature. Specifically, the two-dimensional projection has a first part that bends or curves around point B, a second part that bends or curves around part C, and a third part that bends or curves around point D.

In the illustrated embodiment, the distal end portion 138 is curved such that a center portion of the distal end portion 138 is configured to be disposed closer to a user's head than the remaining portions of the distal end portion 138 when the ear warmer is worn by a user. In an alternative embodiment, the uppermost portion is configured to be disposed closer to the user's head than the lowermost portion when the ear warmer is worn by the user. In a further alternative embodiment, the first ear portion is curved such that the lowermost portion is configured to be disposed closer to the user's head than the uppermost portion when the ear warmer is worn by the user.

Although the first ear portion 130 is described and illustrated as having a particular shape, in other embodiments, the first ear portion has different shapes. Additionally, in one embodiment, the first ear portion is made of a plastic material. In an alternative embodiment, the first ear portion is made of another material, such as a metal.

The first ear portion 130 has an abutting and complimentary fit with the band portion 200. More specifically, returning to FIG. 13, the first ear portion 130 includes coupling portion 164 that extends from an end surface 166 of the first ear portion 130. The coupling portion 164 includes a distal end 165 that defines a surface 165a. In one embodiment, the surface 165a includes one or more ridges or protrusions 165b that engage the recesses 218d as the ear portion rotates. The coupling portion 164 is received in structure 218a. In one embodiment, the end portion of the first ear portion 130 includes surfaces 167a and 167b that compliment and engage surfaces 221a and 221b on the band portion 200 when the ear portion 130 is in its collapsed configuration. The end portion also includes a protrusion 167c with a contact surface 167d that engages the surface 221c and shoulder 221d to form a secondary stop to limit the rotation of the ear portion. In alternative embodiments, the ear portion does not include protrusion 167c and band portion 200 does not include the surface 221c and shoulder 221d. As illustrated in FIG. 20, the surface defined by the distal end 222 of the coupling portion 218 of the band portion 200 abuts the surface defined by the distal end 165 of the coupling portion 164. Also, the end surface 214 of the band portion 200 of the frame 110 abuts the end surface 166 of the first end portion 130. In other words, the band portion 200 abuts the first ear portion 130 and has surfaces, including the surface defined by the distal end 222 of the coupling portion 218 and the end surface 214 of the band portion 200, that fit complimentary to surfaces of the first end portion 130, including the surface defined by the distal end 165 of the coupling portion 164 and the end surface 166 of the first ear portion 130, when the first ear portion 130 is in its collapsed configuration.

Because of abutting and complimentary fit of the band portion 200 and the first ear portion 130, the transition between the outer surface 208 of the band portion 200 and the outer surface 146 of the first ear portion 130 is a smooth transition or a substantially smooth transition. In other words, the outer surface 208 of the band portion 200 and the outer surface 146 of the first ear portion 130 form a substantially continuous surface when the ear warmer is in the expanded configuration. With the exception of the inner surface, the same is true for the remaining surfaces of the band portion 200 and the first ear portion 130. Specifically, the upper surface 210 of the band portion 200 and the upper surface 148 of the first ear portion 130 form a substantially continuous surface. The lower surface 212 of the band portion 200 and the lower surface 150 of the first ear portion 130 form a substantially continuous surface.

In one embodiment, the coupling portions of the ear portion and the band portion is located on the inner surface. In an alternative embodiment, the inner surface of the ear portion and the inner surface of the band portion form a substantially continuous surface. Alternatively, the coupling portions of the band portion and the ear portion are located at different locations.

The substantially continuous surface formed by the upper surface 210 of the band portion 200 and the upper surface 148 of the first ear portion 130 extends from the first ear portion 130 to the second ear portion 190. The substantially continuous surfaces formed by the lower, upper, and inner surfaces of the band portion 210 and the first ear portion 130 also extend to the respective surfaces of the second ear portion. Thus, the upper surface of the ear warmer 100, the lower surface of the ear warmer 100, and the outer surface of the ear warmer 100 collectively form a smooth contour. In alternative embodiments any combination of the corresponding surface, outer surface, upper surface and lower surface of any of the frame components can form a substantially continuous surface.

In one embodiment, a screw (not illustrated) is used to pivotally couple the first ear portion 130 to the band portion 210. A first end of the screw extends from the inner side 144 of the first ear portion 130 and a second end of the screw is disposed within the band portion 200 and is not outwardly visible. In other words, only a single end of the screw is exposed (i.e., disposed outside of the frame 110 of the ear warmer 100). In alternative embodiments, a rivet, a pin, a brad, or any other coupling device is used to pivotally couple the ear portions 130 and 190 to the band portion 200.

FIGS. 10 though 12 illustrate the frame 110 of the ear warmer 100 in a collapsed configuration. The first ear portion 130 and the second ear portion 190 are disposed adjacent to and substantially within the same plane 195 as the band portion 200 when the frame 110 is in its collapsed configuration. The coupling arrangement between the band portion 200 and the ear portions (as described in detail above) allow the ear portions 130 and 190 to pivot into and out of the collapsed configuration. As illustrated in FIG. 12, the ear warmer 100 has a low profile when in its collapsed configuration. In one embodiment, the oblique plane defined by the band portion 200 allows the ear portion 130 and 190 to move in a way that contributes to this overall low profile. For example, the oblique plane allows the ear portions to rotate about the pivot connection while being substantially within or proximate the same plane as the band portion 200.

Ear warmer 100 is configured to allow a predetermined range of motion between the expanded configuration and the collapsed configuration. In one embodiment, this range of motion does not include movement from the expanded configuration to a different collapsed configuration, for example, where the ear portions of the frame are disposed on a side of the band opposite from their position in the collapsed configuration within the range of motion. In one embodiment, two different mechanisms each produce a respective stop that defines a respective end point of the range of motion (as discussed below).

In an alternative embodiment, the ear portions can rotate continuously and are not limited to a particular range. Alternatively, the ear portions can be slidably coupled to the band portion, or can rotate about another axis than that described above.

As illustrated in FIGS. 22 and 23, it is not necessary that the frame be separate items. In FIGS. 22 and 23, the frames 270 and 280, respectively, are of a unitary or monolithic structure. In these embodiments, the band portions 272 and 286, respectively, do not have adjustable lengths. In a further alternative embodiment, the band portion is an adjustable band. In yet a further alternative embodiment, the band portion of the frame includes several different and separate items.

Figure 24:
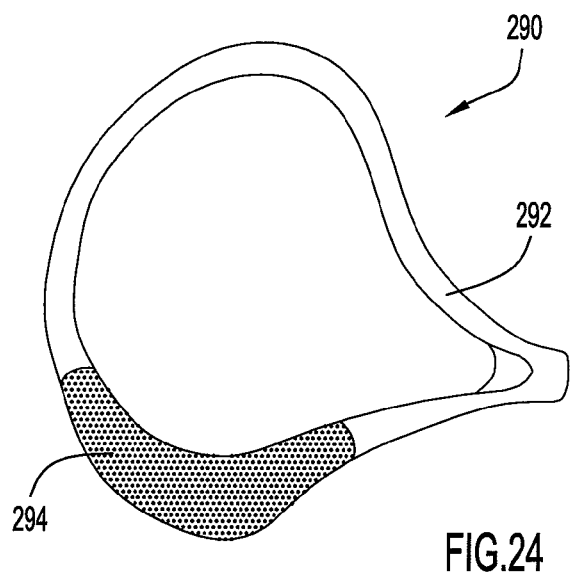
FIG. 24 is a side view of an ear portion according to another embodiment of the invention.
Figure 25:
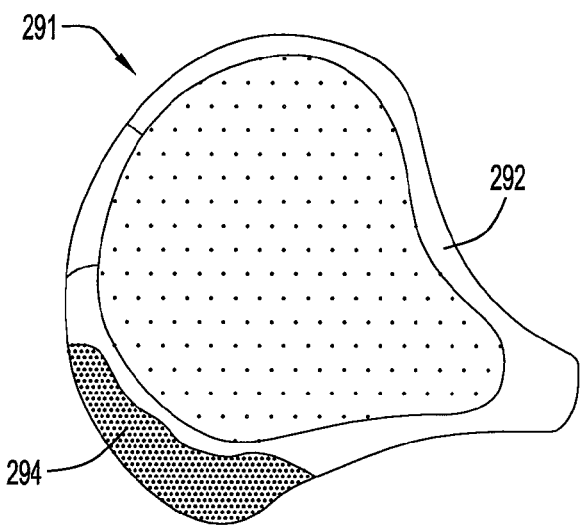
FIG. 25 is a side view of an ear portion according to another embodiment of the invention.

Alternative embodiments of ear portions are illustrated in FIGS. 24 and 25. In these embodiments, the ear portions may be formed of a first material and a second material that is different than the first material. In FIGS. 24 and 25, the ear portions 290 and 291, respectively, are made of a first material 292 and a second material 294. For example, the first material 292 may be any type of plastic and the second material 294 may be any type of resilient material, such as rubber. The resilient material 294 provides for an increased gripping surface for contact with the user or other article. The resilient material 294 also increases the distribution of the application of clamping or gripping force of the ear warmer on the user's head. In FIG. 24, the second material extends an entire width of a portion of the ear portion 290, whereas in FIG. 25, the second material only extends across a portion of width of a portion of the ear portion 292.

In alternative embodiments, the recess or opening in the ear portion in which the second material is disposed can have any size or configuration. The location of the recess or opening for the second material can vary along the ear portion. As previously discussed, the band portion of an ear warmer can also include a portion of a first material and a portion of a second material that is different from the first material.

As illustrated in FIG. 1, the ear warmer 100 includes fabric members 230 and 250. The fabric members 230 and 250 are coupled to the frame 110 of the ear warmer 100. The fabric members 230 and 250 are configured to substantially cover at least a portion of the ear portions 130 and 190 of the ear warmer 100. Various configurations of the fabric members are described below.

FIG. 26 shows a side view of a portion of an ear warmer according to an embodiment of the invention. In this embodiment, the frame 310 includes an ear portion 330. A fabric member 350 is fixedly coupled to the ear portion 330 of the frame 310. For example, the fabric member 350 can be fixedly coupled to the ear portion 330 of the frame 310 by any technique or method, including radio frequency (RF) welding, ultrasonic welding, or an adhesive such as glue. For example, the perimeter portion 352 of the fabric member 350 can be fixedly coupled to or proximate to the perimeter portion 332 of the ear portion 330 of the frame 310. The term "perimeter portion" is intended herein to include the perimeter or a portion offset from and proximate to the perimeter of a membrane, member or portion. Following the example shown in FIG. 26, a weld, adhesive or connector can be located along the actual perimeter of the fabric member 350 and a portion of the ear portion 330 of the frame 310 offset from and proximate to the perimeter of the ear portion 330.

In another embodiment, the fabric member includes binding coupled along at least a portion of the perimeter of the fabric member. In such an embodiment, the binding can be coupled to the frame using the techniques identified above. Alternatively, the fabric member can be coupled to the frame. In this embodiment, the binding provides additional support and cushioning to the user. Additionally, the binding provides a seal between the ear warmer and a user's head.

Figure 26A:
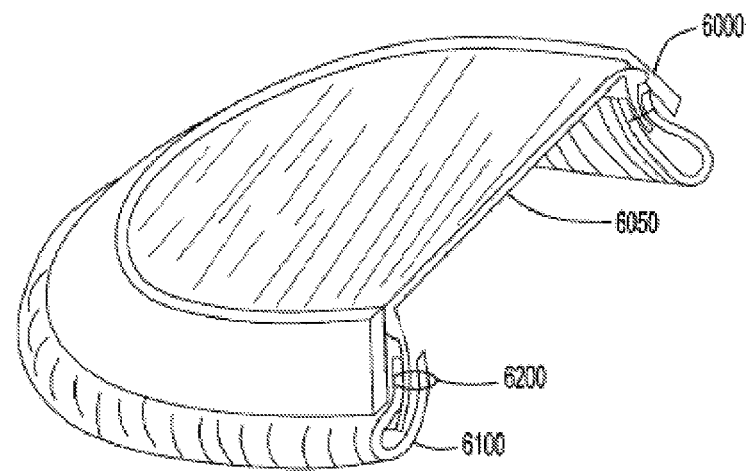
FIGS. 26A and 26B are partial cross-sectional views of an embodiment of a portion of an ear warmer according to an embodiment of the invention.
Figure 26B:

Referring to FIGS. 26A and 26B, which are partial cross-sectional views, an embodiment of an ear portion is illustrated. In this embodiment, the frame 6000, such as an ear portion, includes a fabric member 6050 coupled thereto. In one embodiment, fabric member 6050 includes a binding 6100 coupled thereto in any conventional manner. For example, the binding 6100 can be stitched or sewn to the fabric member 6050 by seam 6200. Fabric member 6050 can be coupled to the frame member 6000 using any conventional technique, including an adhesive, welding, such as RF or ultrasonic welding, or the like. In one embodiment, the binding 6100 is configured so that a portion of it is disposed adjacent to the innermost surface of the frame member 6000. The binding 6100 provides added cushioning, which provides a more comfortable fit. The binding 6100 also provides a better seal against a user's head to improve temperature control by preventing external air from entering any space between the ear portion and the user's head. In an alternative embodiment, the binding can be replaced by another piece of fabric material, a piece of foam, or any other structure that would assist with the cushioning and sealing functions above.

FIGS. 27 through 32 show examples of a fabric member that can be removably coupled to the ear portion of the frame. Although these figures show the fabric member being removably coupled to the ear portion of frame via press-fit connections, tongue-and-groove connections, clip-on connections and slide-and-lock connections, other types of the removable connections are also possible. In other words, FIGS. 27 through 32 merely provide examples of removable connections and other types of removable connections are possible.

FIGS. 27 and 28 show a side view and cross-section view along line 28-28 in FIG. 27, respectively, of a portion of an ear warmer 400 having a press-fit connection, according to an embodiment of the invention. Ear warmer 400 includes a frame 410 that has an ear portion 430. As shown in FIG. 27, the fabric member 450 can be fixedly coupled to an attachment member 460 along a portion of the perimeter of the fabric member 450. In this embodiment, the attachment member 460 can be made of, for example, plastic defining an opening 462 along its length and directed inwardly. As shown in FIG. 28, the opening 462 is configured such that the attachment member 460 forms a press fit over a portion of the perimeter 432 of the ear portion 430 of the frame 410. This configuration allows the fabric member 450 to be removably attached to the ear portion 430 of the frame 410. To fit over the outer side of the perimeter 432 of the ear portion 430 of the frame 410, the fabric member 450 can be made from an elastic material that is stretched when the fabric member 450 and attachment member 460 are coupled onto the ear portion 430 of the frame 410. Alternatively, the fabric member 450 can be larger than the ear portion 430 of the frame 410 so that the fabric member 450 can extend over the perimeter 432 of the ear portion 430 of the frame 410 when being configured onto the ear portion 430 of the frame 410.

Figure 29:
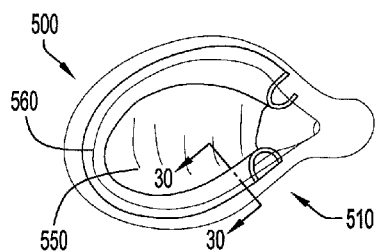
FIGS. 29 and 30 are a side view and cross-section view along line 30-30, respectively, of a portion of an ear warmer having a press-fit connection, according to another embodiment of the invention.
Figure 30:
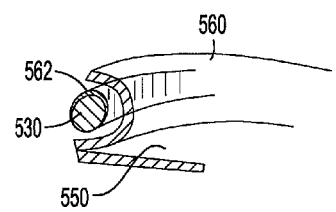

FIGS. 29 and 30 show a side view and cross-section view along line 30-30 in FIG. 29, respectively, of a portion of an ear warmer 500 having a press-fit connection, according to another embodiment of the invention. The ear warmer 500 includes a frame 510 that has an ear portion 530. Similar to that embodiment shown in FIGS. 27 and 28, in FIG. 30, the fabric member 550 can be fixedly coupled to an attachment member 560 along a portion of the perimeter of the fabric member 550. In this embodiment, however, the opening 562 defined by the attachment member 560 along its length is directed outwardly. As shown in FIG. 30, the opening 562 has a size such that the attachment member 560 forms a press fit along a portion of the ear portion 530 of the frame 510. In particular, the ear portion 530 of the frame 510 defines an interior region defined by a perimeter. The attachment member 560 removably attaches the fabric member 550 to a portion of this perimeter of the interior region. The attachment member 560 has sufficient strength and rigidity so that the attachment member 560 is inserted or "popped" into an opening defined in the ear portion 530.

Figure 31:
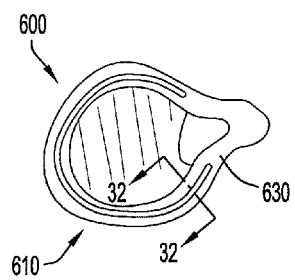
FIGS. 31 and 32 are a side view and cross-section view along line 32-32, respectively, of a portion of an ear warmer having a tongue-and-groove connection, according to an embodiment of the invention.
Figure 32:
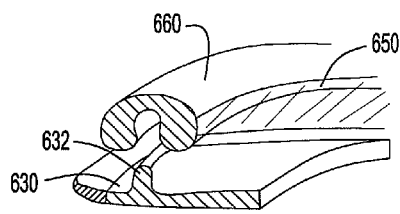

FIGS. 31 and 32 show a side view and cross-section view along line 32-32 in FIG. 31, respectively, of a portion of an ear warmer 600 having a tongue-and-groove connection, according to an embodiment of the invention. In this embodiment, the ear warmer 600 includes a frame 610 that has an ear portion 630. As shown in FIG. 32, the fabric member 650 can be coupled (e.g., fixedly coupled) to an attachment member 660 along a portion of the perimeter of the fabric member 650. In this embodiment, the attachment member 660 has a surface with a groove structure formed therein, and complimentary fits onto or receives the tongue-like portion 632 of the ear portion 630 of the frame 610. This mating of the attachment member 660 and the ear portion 630 allows the fabric member 650 to be removably attached to the ear portion 630 of the frame 610. The tongue-like portion 632 of the ear portion 630 of the frame 610 can be monolithically formed with the remaining portions of the ear portion 630 of the frame 610. Alternatively, a tongue-like member can be coupled (e.g., fixedly coupled) to the ear portion of the frame by welding or an adhesive. In another alternative embodiment, the tongue-like structure can be coupled (e.g., fixedly coupled) to the fabric member and the groove-like structure can be disposed on the ear portion or the frame, for example, either fixedly coupled to or monolithically formed with the ear portion of the frame.

Figure 33:
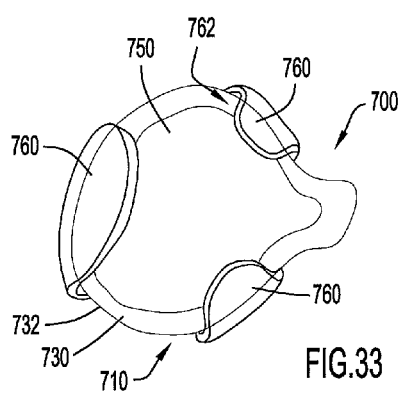
FIG. 33 is a side view of a portion of an ear warmer having a clip-on connection, according to an embodiment of the invention.

FIG. 33 shows a side view of a portion of an ear warmer 700 having a clip-on connection, according to an embodiment of the invention. The ear warmer 700 includes a frame 710 that has an ear portion 730 with a perimeter 732. As shown in FIG. 33, a fabric member 750 can be coupled (e.g., fixedly coupled) to one or more attachment members 760 along various positions of the perimeter of the fabric member 750. More specifically, FIG. 33 shows three attachment members 760 although in other embodiments, one, two, four or more than four attachment members are possible. The various attachment members can be formed integrally or can be coupled together by different structures. Each of the attachment members 760 shown in FIG. 33 has a clip-like structure that defines an opening 762 along its length and is directed inwardly. These attachment members 760 can be made of any material that allows the attachment members 760 to coupled to the frame, including, for example, plastic or metal. The opening 762 of each attachment member 760 is configured such that it forms a complimentary fit over a portion of the perimeter 732 of the ear portion 730 of the frame 710. This mating arrangement of the attachment members 760 and the ear portion 730 allows the fabric member 750 to be removably attached to the ear portion 730 of the frame 710. Similar to the embodiment described above in reference to FIGS. 27 and 28, to fit of the outer side of the perimeter of the ear portion 730 of the frame 710, the fabric member 750 can be made from an elastic material that is stretched when the fabric member 750 and attachment members 760 are coupled onto the ear portion 730 of the frame 710. Alternatively, the fabric member 750 can be larger than the ear portion 730 of the frame 710 so that the fabric member 750 can extend over the perimeter 732 of the ear portion 730 of the frame 710 when being coupled onto the ear portion 730 of the frame 710.

FIGS. 34 through 38 show examples of a fabric member removably coupled to the ear portion of the frame by covering substantially an entirety of the opening on the inner side of the ear portion of the frame and less than an entirety of the opening on the outer side of the ear portion of the frame. More specifically, the ear portion of the frame typically defines an opening through which sound can pass. This opening has an interior portion corresponding to the inner side of the ear portion of the frame and an exterior portion corresponding to the outer side of the ear portion of the frame. As described in more detail in reference to FIGS. 34 through 38, an ear portion of the fabric member can be configured such that it covers the interior portion of the opening substantially in its entirety and covers the exterior portion of the opening in less than its entirety. Covering the interior portion of the opening "substantially in its entirety" is intended to describe embodiments where the entire interior portion of the opening is covered except for minor exceptions such as, for example, small vents.

Figure 34:
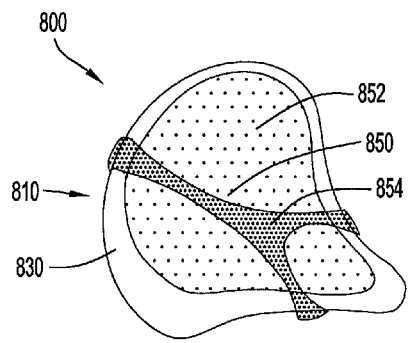
FIG. 34 is a side view of a portion of an ear warmer having a fabric member, according to an embodiment of the invention.

FIG. 34 shows a side view of a portion of an ear warmer 800 having a fabric member 850, according to an embodiment of the invention. The ear warmer 800 includes a frame 810 that has an ear portion 830. In one embodiment, the fabric member 850 includes an ear portion with a heat-retaining fabric 852 on the inner side. The ear warmer 800 can include an elastic fabric or member 854 on the outer side. In one embodiment, the elastic fabric 854 is coupled (e.g., fixedly coupled) to the heat-retaining fabric 852 at three locations. In alternative embodiments, the elastic or rubber fabric can be coupled to the heat-retaining fabric 852 at any number of locations. In one embodiment, the elastic member 854 can be a clip or snap-on structure that clips or clamps the heat-retaining fabric 852 to the ear portion 830. In an alternative embodiment, the elastic member 854 can be a separate piece that can wrap around the inner side and the outer side of a portion of the ear portion 830 and couple the fabric 852 thereto. In another embodiment, the heat-retaining fabric 852 and the elastic fabric 854 are coupled together in a manner other than fixedly coupled, such as removably coupled.

The fabric member 850 can be removably coupled to the ear portion 830 of the frame 810 by stretching the elastic fabric on the outer side of the fabric member 850 so that it can move over the distal end of the ear portion 830 of the frame 810. As shown in FIG. 34, the heat-retaining fabric 852 on the inner side of the fabric member 850 covers the interior portion of the opening of the ear portion 830 of the frame 810 substantially in its entirety while the elastic fabric 854 covers the exterior portion of the opening of the ear portion 830 of the frame 810 in less than its entirety. Any combination of coupling techniques can be used to couple the fabric member 850 to the ear portion 830.

Figure 35:
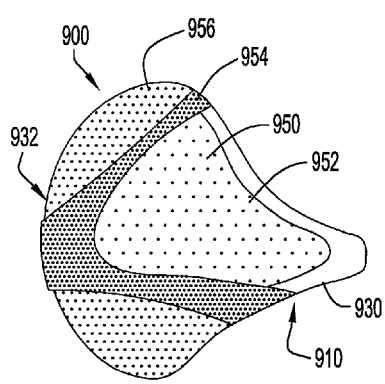
FIG. 35 is a side view of a portion of an ear warmer having a fabric member, according to another embodiment of the invention.

FIG. 35 shows a side view of a portion of an ear warmer 900 having a fabric member 950, according to another embodiment of the invention. As shown in FIG. 35, the ear portion of the fabric member 950 has a heat-retaining fabric 952 on the inner side, and an elastic fabric portion 954 and a heat-retaining portion 956 on the outer side. The elastic fabric can be, for example, a rubber material or a heat-retaining fabric. In this particular embodiment, the outer side of the fabric member 950 is coupled (e.g., fixedly coupled) to the heat-retaining fabric 952 on the inner side along a portion of the perimeter. Thus, the fabric member 950 can be removably coupled to the ear portion 930 of the frame 910 by stretching the elastic fabric 954 on the outer side of the fabric member 950 so that it can move over the distal end 932 of the ear portion 930 of the frame 910. In one embodiment, the fabric 952 and the heat-retaining portion 956 can be formed integrally.

Figure 36:
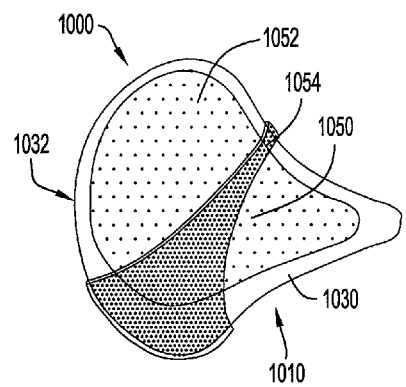
FIG. 36 is a side view of a portion of an ear warmer having a fabric member, according to another embodiment of the invention.

FIG. 36 shows a side view of a portion of an ear warmer 1000 having a fabric member 1050, according to another embodiment of the invention. Fabric member 1050 is coupled in a similar manner as fabric member 850 described above. As shown in FIG. 36, the ear portion of the fabric member 1050 has a heat-retaining fabric 1052 and an elastic fabric 1054. The elastic fabric can be, for example, a rubber material or a heat-retaining fabric. In this particular embodiment, the elastic fabric 1054 on the outer side is coupled (e.g., fixedly coupled) to the heat-retaining fabric 1032 on the inner side at two locations. The fabric member 1050 can be removably coupled to the ear portion 1030 of the frame 1010 by stretching the elastic fabric 1054 on the outer side of the fabric member 1050 so that it can move over the distal end 1032 of the ear portion 1030 of the frame 1010.

Figure 37:
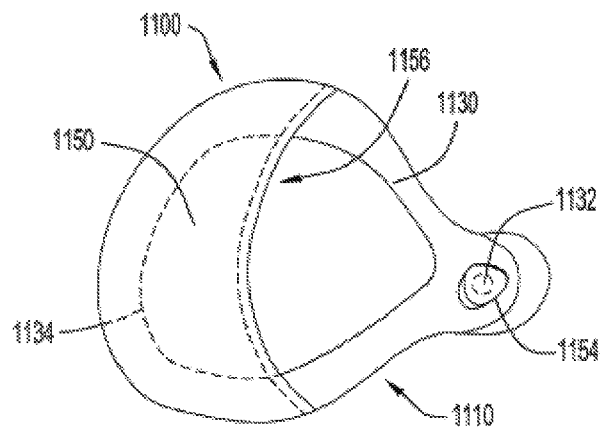
FIG. 37 is a side view of a portion of the ear warmer having a fabric member, according to another embodiment of the invention.
Figure 38:
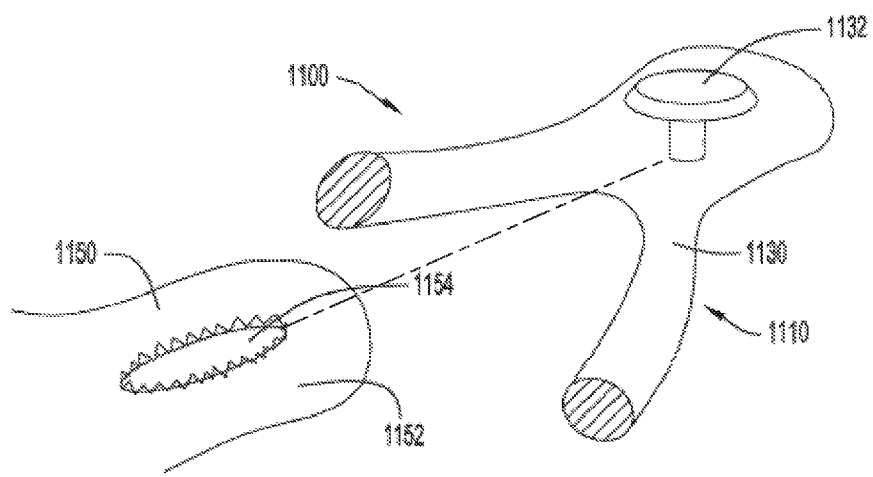
FIG. 38 is a perspective assembly view of the portion of the ear warmer shown in FIG. 37.

FIG. 37 shows a side view of a portion of the ear warmer 1100 having a fabric member 1150, according to another embodiment of the invention. FIG. 38 shows a perspective assembly view of the portion of the ear warmer 1100 shown in FIG. 37. As shown in FIG. 37, the fabric member 1150 (one is shown in FIG. 37 for one ear portion of the frame) has an inner side and an outer side. As shown in FIG. 38, the inner side 1152 of the fabric member 1150 includes a coupling portion 1154 embodied as a button hole. The ear portion 1130 of the frame 1110 includes a coupling portion 1132 embodied as a button and post. The coupling portion 1154 of the fabric member 1150 is configured to mate with the coupling portion 1132 of the ear portion 1130 of the frame 1110 such that the fabric member 1150 is removably coupled to the ear portion 1130 of the frame 1110. As shown in FIGS. 37 and 38, the coupling portion 1132 of the frame 1110 is disposed on the inner side of the frame.

More specifically, the inner side and outer side of the fabric member 1150 form a receptacle 1156 into which the distal end 1134 of the ear portion 1130 of the frame 1110 can be removably disposed. This side of the ear portion of the fabric member 1150 is referred to herein as the distal end. The proximate end of the fabric member 1150 is also removably coupled to the ear portion 1130 of the frame 1110, as discussed above, by the coupling portion 1154 of the fabric member 1150 fitting into the coupling portion 1132 of the ear portion 1130 of the frame 1110. Thus, the overall fabric member 1150 can be coupled to the ear portion 1130 of the frame 1110 by coupling the distal end of the fabric member 1150 to the distal end 1134 of the ear portion 1130 of the frame 1110, and then coupling the proximate end of the fabric member 1150 to the proximate end of the ear portion 1130 of the frame 1110. The fabric member 1150 can be removed from the frame 1110 by the reverse process.

Although the coupling portion 1132 of the ear portion 1130 of the frame 1110 is shown in FIGS. 37 and 38 as protruding from the inner side of the frame, in alternative embodiments, the coupling portion of the frame extends from a recess in the inner side of the frame. Thus, the distal end of the coupling portion of the frame corresponds to the remaining inner surface of the ear portion of the frame in that region and in general they form a smooth surface having the recess.

In alternative embodiments, the coupling portion of the ear portion of the frame and the coupling portion of the ear portion of the fabric member can be disposed on any part of the frame, including the outer side of the frame. In such an alternative embodiment, the outer side of the ear portion of the frame is substantially covered in its entirety and the inner side of the ear portion of the frame covered in less than its entirety.

In an alternative embodiment, the ear portion of the frame and the ear portion of the fabric member can be coupled together using any conventional technique, such as hook-and-loop fasteners, snap-fit connections, and button-and-hole arrangements having the hole on the frame.

Figure 39:
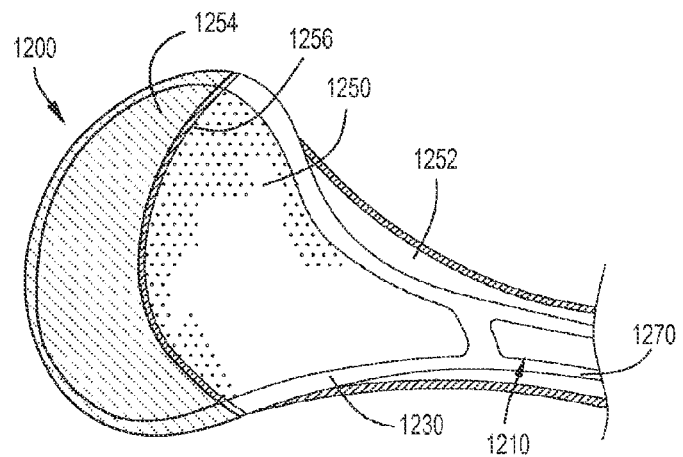
FIG. 39 is a perspective view of a portion of an ear warmer having a fabric member covering at least a portion of the inner side of the frame, according to an embodiment of the invention.
Figure 40:
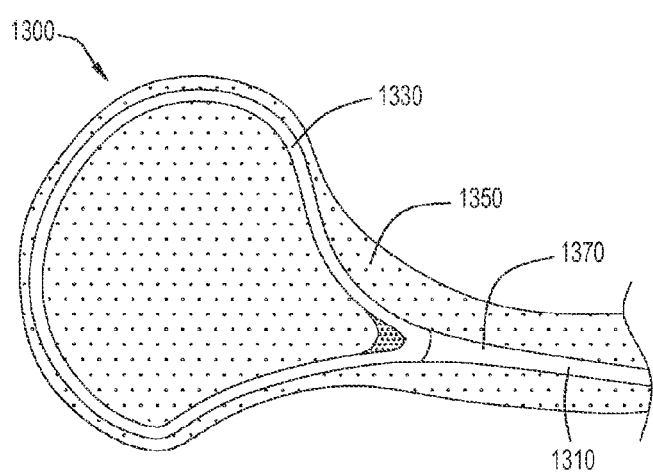
FIG. 40 is a perspective view a portion of an ear warmer having a fabric member covering at least a portion of the inner side of the frame, according to another embodiment of the invention.

FIGS. 39 and 40 show examples of a fabric member removably coupled to the frame by covering substantially an entirety of the inner side of the frame and less than an entirety of the opening on the outer side of each ear portion of the frame. More specifically, the examples shown in FIGS. 39 and 40 show a fabric member that substantially covers the entirety of the inner side of the frame including its ear portions and band portion while covering less than the entirety of the outer side of the frame.

FIG. 39 shows a perspective view of a portion of an ear warmer 1200 having a fabric member 1250 covering the inner side of the frame 1210, according to an embodiment of the invention. As shown in FIG. 39, the fabric member 1250 has an inner-side portion 1252 and an outer-side portion 1254. The inner-side portion 1252 of the fabric member 1250 corresponds to both ear portions 1230 of the frame 1210 (of which only one is shown in FIG. 39) and the band portion 1270 of the frame 1210 (only a portion of which is shown in FIG. 39). In this embodiment, the outer-side portion 1254 of the fabric member 1250 can be extended over the distal end of the ear portions 1230 of the frame 1210. Thus, the distal end of the ear portions 1230 of the frame 1210 can be retained in a receptacle 1256 formed by the inner-side portion 1252 and the outer-side portion 1254 of the fabric member 1230. The outer-side portion 1252 of the fabric member 1250 can be made of, for example, an elastic fabric that allows the fabric member 1250 to be stretched over the distal end of the ear portions 1230 of the frame 1210 to insert and remove the frame 1210 from the fabric member 1250. In alternative embodiments, the fabric members can be bound, sewn, welded, coupled inside out, or monolithically formed (i.e., unitary construction).

FIG. 40 shows a perspective view a portion of an ear warmer 1300 having a fabric member 1350 covering the inner side of the frame 1310, according to another embodiment of the invention. As shown in FIG. 40, the fabric member 1350 has only an inner-side portion. The inner-side portion of the fabric member 1350 corresponds to both ear portions 1330 of the frame 1310 (of which only one is shown in FIG. 40) and the band portion 1370 of the frame 1310 (only a portion of which is shown in FIG. 40). In this embodiment, the inner-side portion of the fabric member 1350 can be fixedly coupled to the frame 1310 as described above in reference to FIG. 26, or can be removably coupled to the frame, for example, as described above in reference to FIGS. 31 and 32.

Although not explicitly shown in FIGS. 39 and 40, in alternative embodiments, the fabric member can cover substantially the entirety of the inner side of the frame while being removably coupled to the frame as described above, for example, in reference to FIGS. 27 through 30, 33 and 38. In a further alternative embodiment, the fabric member can have a first portion that covers one of the ear portions of the frame and a second portion that covers the other of the ear portions of the frame. In this embodiment, the first portion of the fabric member can be coupled to the second portion of the fabric member via any type of coupling device, such as hook and loop configuration.

Figure 41:
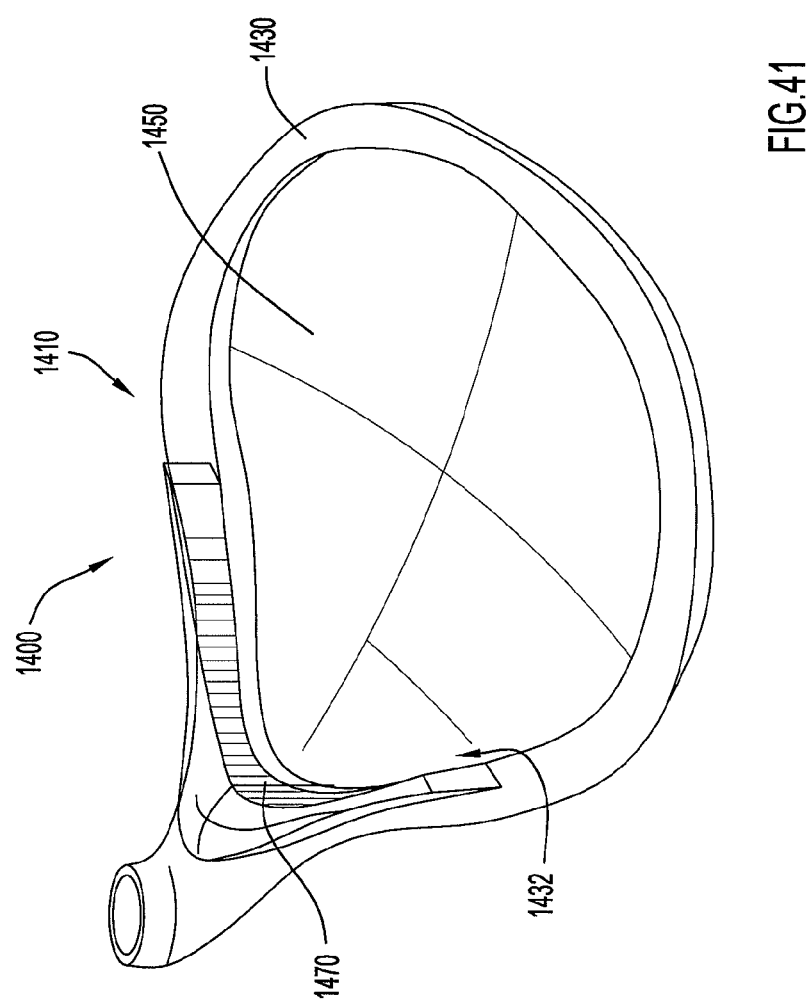
FIG. 41 is a perspective view a portion of an ear warmer having a fabric member and a support member, according to another embodiment of the invention.
Figure 42:
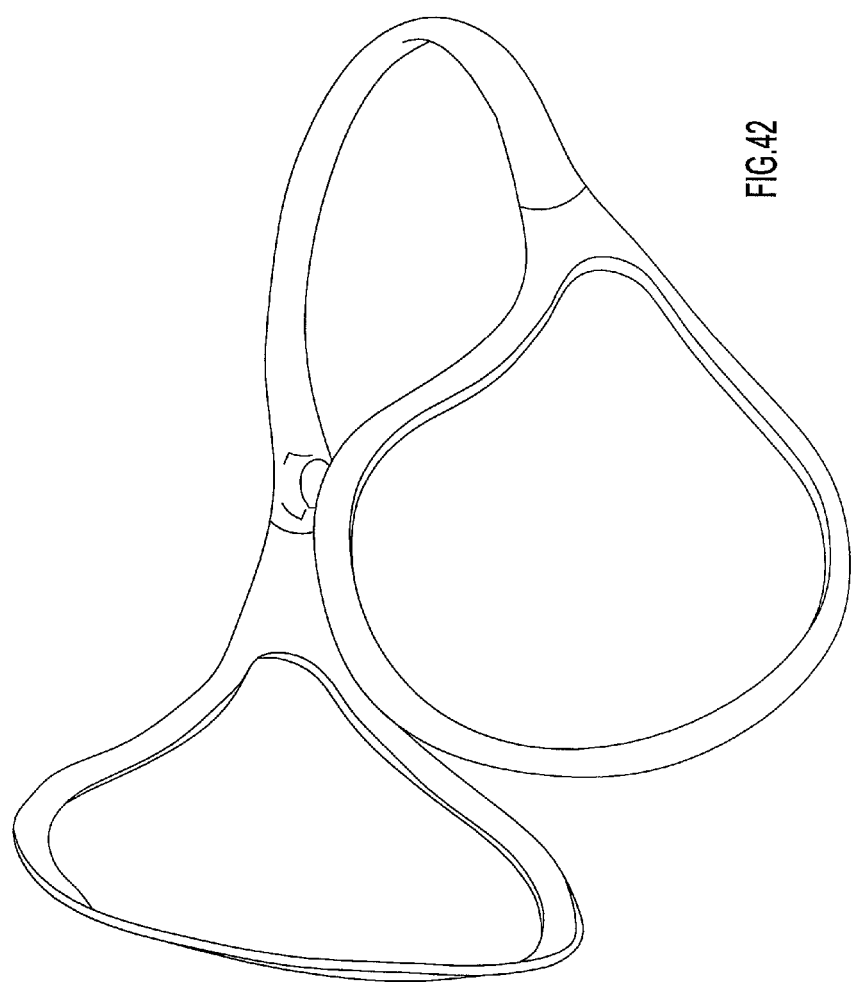
FIG. 42 is a perspective view of a frame of an ear warmer according to an embodiment of the invention.
Figure 43:
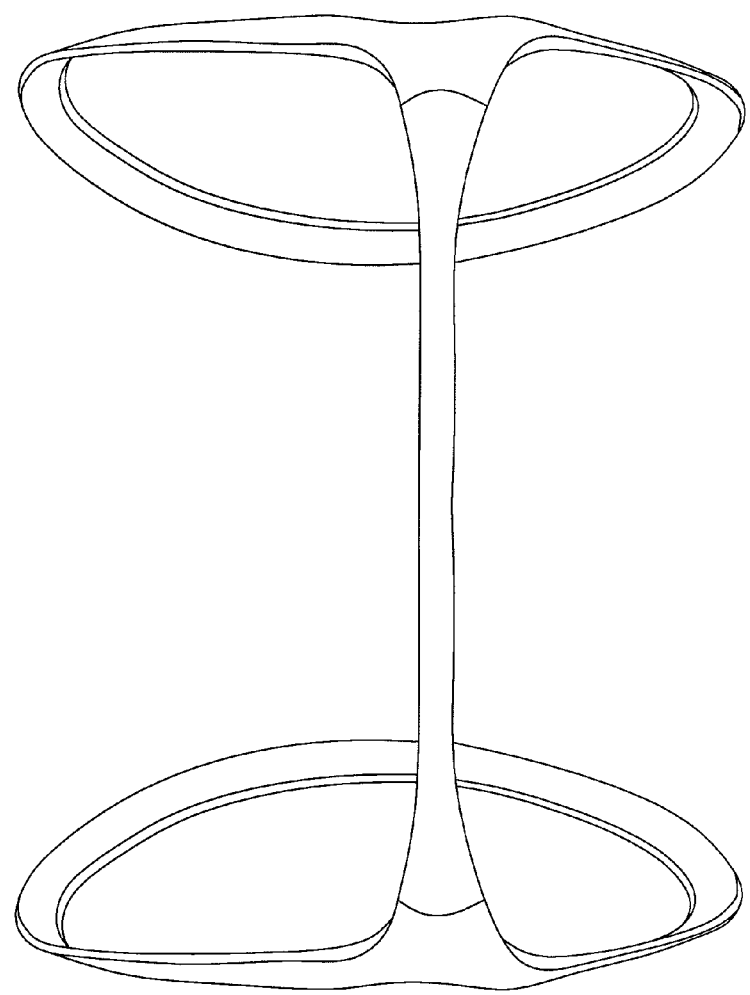
FIG. 43 is a rear view of the frame illustrated in FIG. 42.
Figure 44:
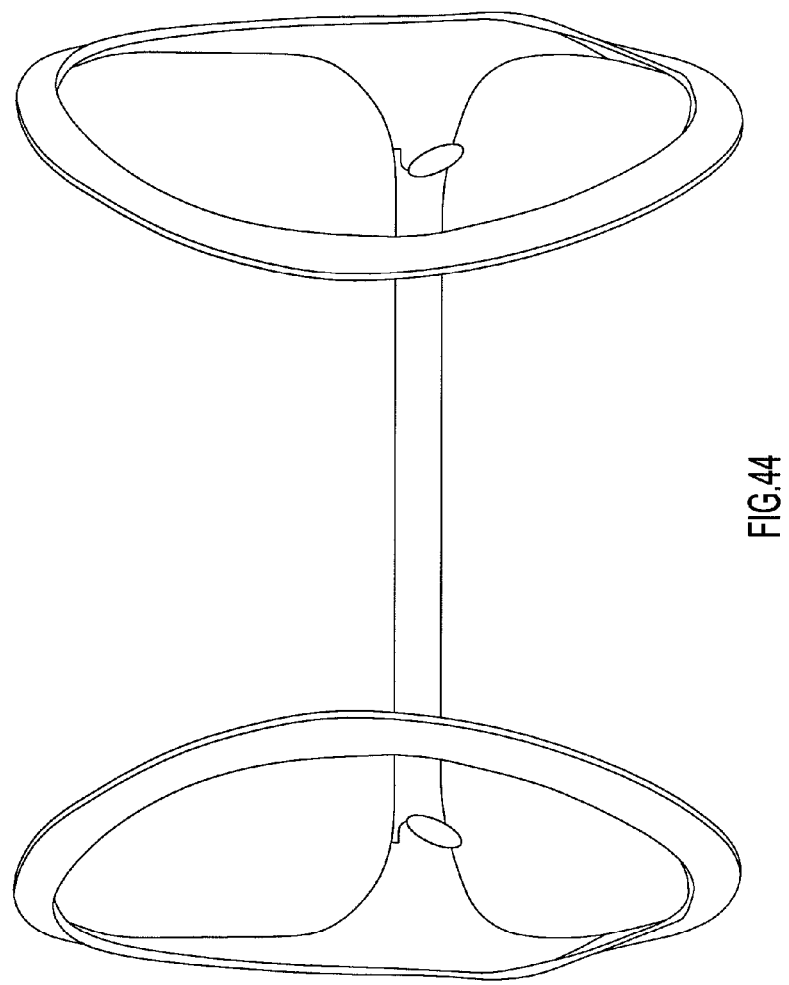
FIG. 44 is a front view of the frame illustrated in FIG. 42.
Figure 45:
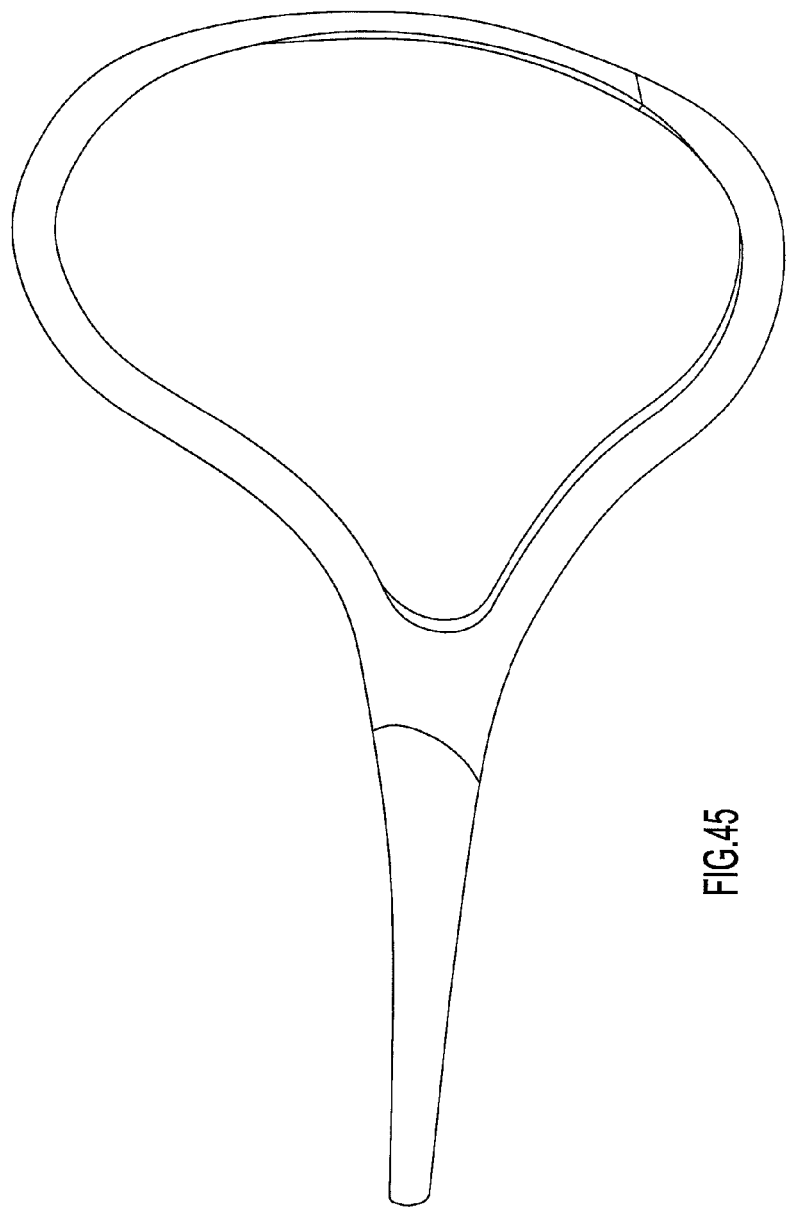
FIG. 45 is a right side view of the frame illustrated in FIG. 42.
Figure 46:
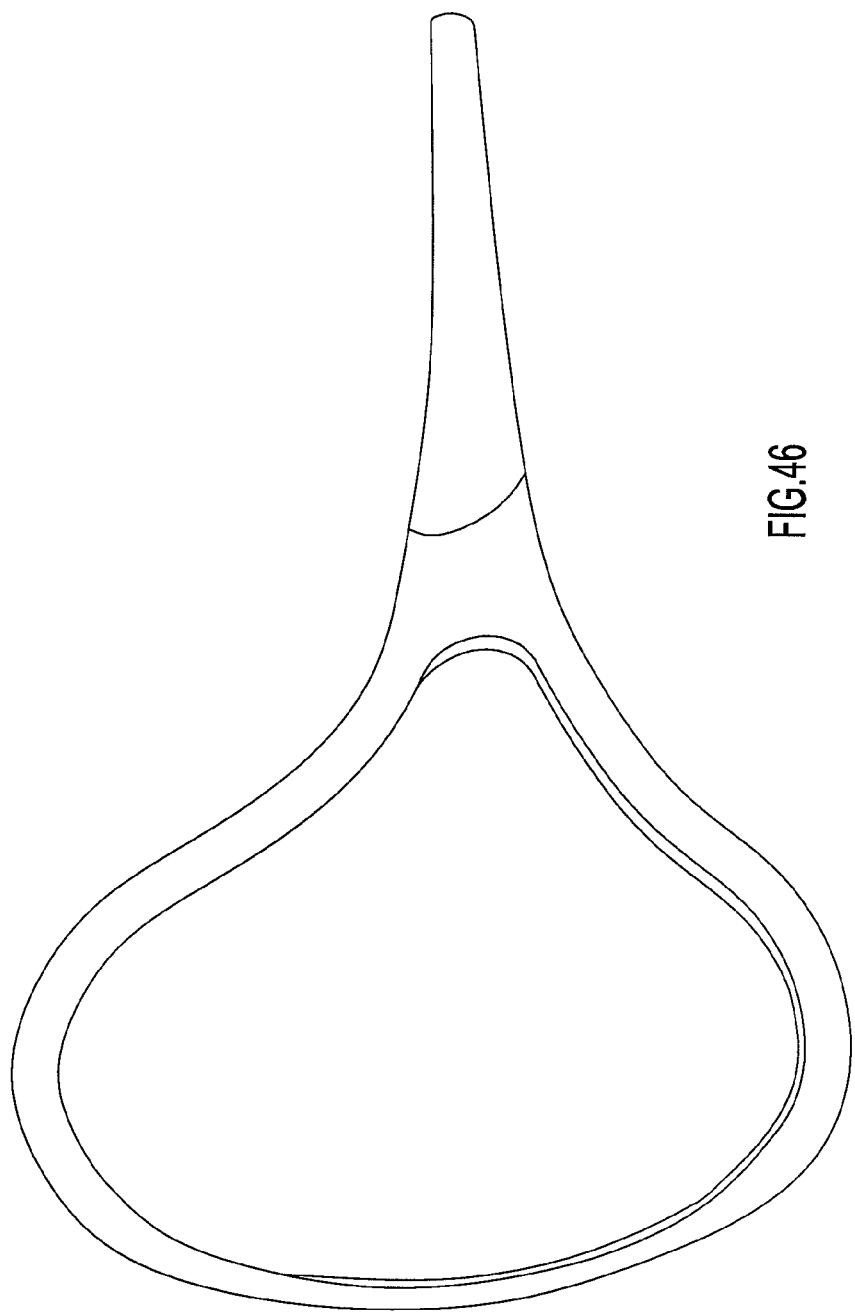
FIG. 46 is left side view of the frame illustrated in FIG. 42.
Figure 47:
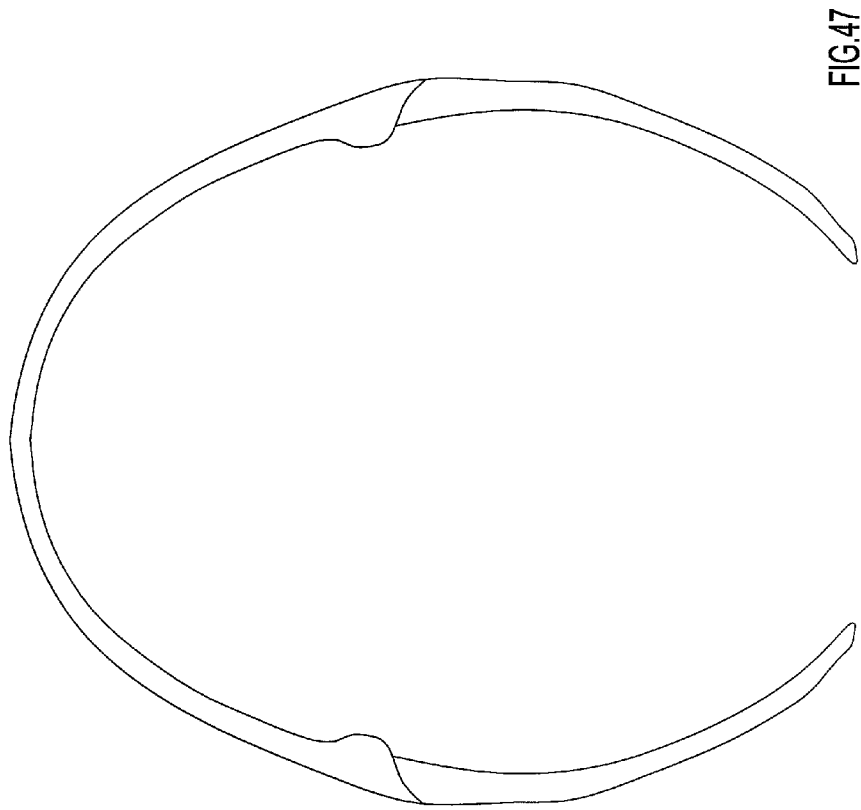
FIG. 47 is a top view of the frame illustrated in FIG. 42.
Figure 48:
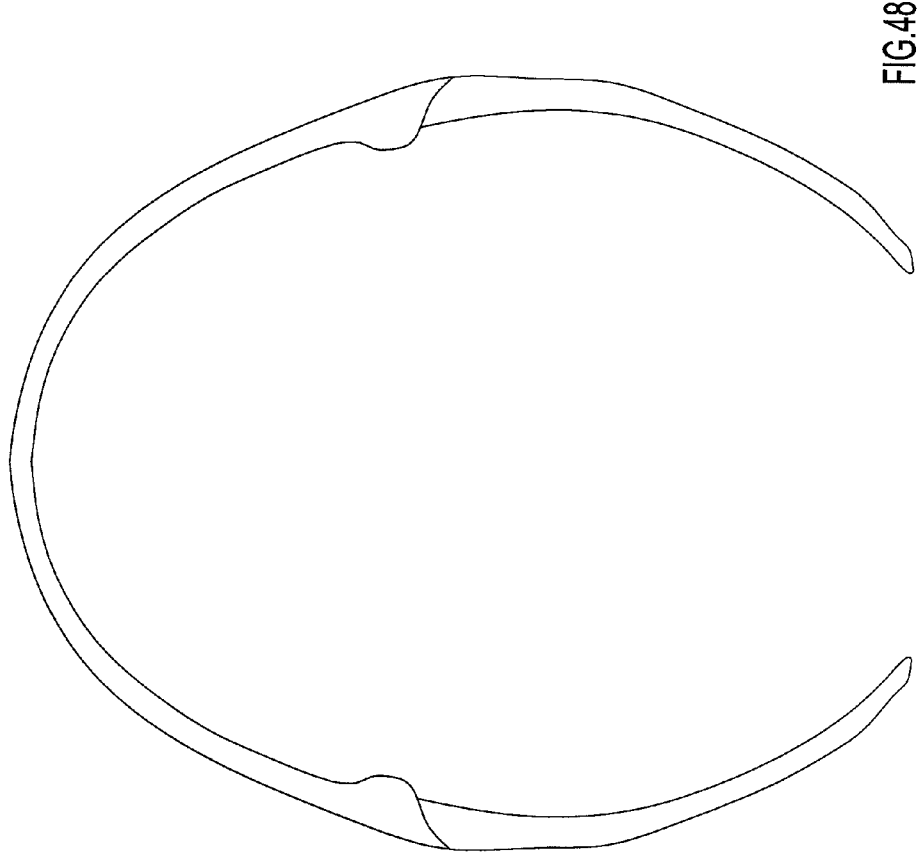
FIG. 48 is a bottom view of the frame illustrated in FIG. 42.

FIG. 41 shows a perspective view a portion of an ear warmer 1400 having a fabric member 1450 and a contact member 1470, according to another embodiment of the invention. As shown in FIG. 41, the frame 1410 includes a contact member 1470 disposed on the inner side 1432 of the ear portion 1430 of the frame 1410. The contact member 1470 is configured to provide support and comfort to the user of the ear warmer 1400 by contacting the portion of the user's head behind the user's ears. Additionally, the contact member 1470 provides a seal between the ambient conditions and the user's ear. In other words, the contact member fills the gap between the frame 1410 of the ear warmer 1400 and the user's head. In this embodiment, the contact member 1470 extends along a portion of the inner side 1432 of the ear portion 1430. In alternative embodiments, the contact member extends along substantially the entire inner side of the ear portion.

In one embodiment, the fabric member includes a receptacle that receives the contact member. In alternative embodiments, the contact member is otherwise coupled to the fabric member, such as via an adhesive. In an alternative embodiment, the contact member is coupled to another portion of the ear warmer, such as the band portion of the frame.

In one embodiment, the contact member can be made of a pre-formed foam or rubber material that is covered in fabric. The contact can be slightly deformed and inserted into the opening of the ear portion. The contact member is then released and retained via the opening.

In one embodiment, the contact member is a foam material or rubber material that is not covered in fabric. In an alternative embodiment, the contact member is made of a material other than foam. In a further alternative embodiment, the contact member is a foam material that is covered with a material other than fabric.

While the invention has been described in detail and with references to specific embodiments thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents. For example, although the fabric member is generally described above as being disposed on the inner side of the ear portion of the frame, the fabric member can instead be disposed on the outer side of the ear frame. In some such embodiments, the fabric member can cover substantially an entirety of the opening on the outer side of the ear portion of the frame and less than an entirety of the opening on the inner side of the ear portion of the frame.

What is claimed is:
1. An apparatus, comprising:
a frame configured to be worn around a back of a head, the frame including:
  a band portion, and
  an ear portion movably coupled to the band portion, the ear portion having an opening formed therein, the ear portion having a first side and a second side opposite the first side, the first side disposed between the second side and the head when the frame is worn around the back of the head;
a membrane configured to be coupled to the ear portion, when the membrane is coupled to the ear portion, the membrane covering an area of the first side of the ear portion and an area of the second side of the ear portion smaller than the area of the first side of the ear portion, the membrane covering less than an entirety of the opening on the second side of the ear portion; and
an attachment member coupled to at least a portion of a perimeter of the membrane, the attachment member configured to be directly coupled to at least a portion of the perimeter of the ear portion.

2. The apparatus of claim 1, wherein the ear portion has a proximal perimeter portion and a distal perimeter portion, the proximal perimeter portion disposed between the distal perimeter portion and the band portion, when the membrane is coupled to the ear portion, the membrane covering the distal perimeter portion but not the proximal perimeter portion.

3. The apparatus of claim 1, wherein:
the membrane has a first side and a second side opposite the first side, the first side of the membrane disposed between the second side of the membrane and the head when the membrane is coupled to the ear portion and the frame is worn around the back of the head, and
a portion of the second side of the membrane contacting a portion of the first side of the ear portion when the membrane is coupled to the ear portion.

4. The apparatus of claim 1, wherein the area of the second side of the ear portion is exposed when the membrane is coupled to the ear portion and the frame is worn around the back of the head.

5. The apparatus of claim 1, wherein:
the attachment member is configured to cover a portion of the second side of the ear portion when the membrane is coupled to the ear portion.

6. The apparatus of claim 1, wherein the membrane does not cover any portion of the second side of the ear portion.

7. The apparatus of claim 1, wherein the attachment member is substantially semicircular.

8. The apparatus of claim 1, wherein:
the attachment member is substantially semicircular;
a first portion of the attachment member is disposed on the first side of the ear portion when the membrane is coupled to the ear portion; and
a second portion of the attachment member is disposed on the second side of the ear portion when the membrane is coupled to the ear portion.

9. The apparatus of claim 1, wherein:
a proximal portion of the ear portion is coupled to the band;
a first portion of the ear portion includes the proximal portion and an uppermost portion of the ear portion, the first portion of the ear portion spanning an entirety between the proximal portion and the uppermost portion of the ear portion;
the first portion of the ear portion has a first average radius of curvature;
a second portion of the ear portion includes the proximal portion and a lowermost portion of the ear portion, the second portion of the ear portion spanning an entirety between the proximal portion and the lowermost portion of the ear member; and
the second portion of the ear member has a second average radius of curvature, the second average radius of curvature less than the first average radius of curvature.

10. The apparatus of claim 9, wherein:
a third portion of the ear portion is disposed between the uppermost portion of the ear portion and a distal portion of the ear portion;
a fourth portion of the ear portion is disposed between the lowermost portion and the distal portion of the ear portion; and
the membrane is configured to be removeably coupled to the third portion of the ear portion and the fourth portion of the ear portion.

11. The apparatus of claim 1, wherein the attachment member defines an opening configured to directly receive an edge of the ear portion, the edge of the ear portion disposed between the first side and the second side of the ear portion.

12. The apparatus of claim 1, wherein:
the perimeter of the ear portion is an outer perimeter of the ear portion;
the attachment member defines an opening directed inwardly towards the ear portion such that at least a portion of the attachment member is disposed outwardly of the outer perimeter of the ear portion when the membrane is coupled to the ear portion.

13. The apparatus of claim 1, wherein:
the attachment member partially covers without completely surrounding a cross section of the ear portion when the membrane is coupled to the ear portion.

14. The apparatus of claim 1, wherein:
a first portion of the ear portion is disposed between the first side of the ear portion and the second side of the ear portion;
the attachment member is configured to directly cover the first portion of the ear portion when the membrane is coupled to the ear portion; and
a second portion of the ear portion is disposed between the first side of the ear portion and the second side of the ear portion, the second portion of the ear portion opposite the first portion of the ear portion; and
the second portion of the ear portion is not covered by the attachment member when the membrane is coupled to the ear portion.

15. The apparatus of claim 1 wherein:
the attachment member defines an opening;
an inner surface of the attachment member is disposed within the opening, at least a portion of the inner surface of the attachment member configured to be in direct contact with the portion of the perimeter of the ear portion when the membrane is coupled to the ear portion; and
an outer surface of the attachment surface is opposite the inner surface, the attachment member directly coupled to the portion of the perimeter of the membrane via the outer surface.

16. An apparatus, comprising:
a frame configured to be worn around a back of a head, the frame having a band portion, a first ear portion, and a second ear portion,
the band portion having a first end and a second end opposite to the first end,
the first ear portion movably coupled to the first end of the band portion and selectively disposable in a deployed position and in a collapsed position, the first ear portion having a first side and a second side opposite the first side, the first side of the first ear portion disposed between the second side of the first ear portion and the head when the frame is worn around the back of the head, an edge of the first ear portion defining an opening when the frame is worn around the back of the head,
the second ear portion coupled to the second end of the band portion;
a membrane removably coupleable to the first ear portion via a first attachment portion, the membrane configured to cover substantially an entirety of the opening on the first side of the first ear portion and less than an entirety of the edge on the second side of the first ear portions; and
a second attachment portion directly coupled to the membrane, the membrane removably coupleable to the second ear portion via the second attachment portion, the second attachment portion configured to be directly coupled to an edge of the second ear portion when the membrane is coupled to the second ear portion.

17. The apparatus of claim 16, wherein the first attachment portion is configured to engage at least a portion of a perimeter of the first ear portion, the second attachment portion is configured to engage at least a portion of a perimeter of the second ear portion.

18. The apparatus of claim 16, further comprising:
an elastic membrane, the elastic membrane being in a stretched configuration when the first attachment member is coupled to the first ear portion.

19. The apparatus of claim 16, wherein the membrane is configured to cover an area of the first side of the first ear portion and an area of the second side of the first ear portion smaller than the area of the first side of the first ear portion.

20. An apparatus, comprising:
a frame configured to be worn around a back of a head, the frame having a band portion, a first ear portion, and a second ear portion,
the first ear portion having a first side and a second side opposite the first side of the first ear portion, the first side of the first ear portion disposed between the second side of the first ear portion and the head when the band portion is worn around the back of the head, an edge of the first ear portion defining an opening, the first ear portion being pivotally coupled to the band portion, an end portion of the first ear portion having an abutting and complimentary fit with an end portion of the band portion, the first ear portion being movable relative to the band portion between a deployed position and a collapsed position, a surface of the first ear portion and a surface of the band portion forming a substantially continuous surface when the first ear portion is in the deployed position, the second ear portion having a first side and a second side opposite the first side of the second ear portion, the first side of the second ear portion disposed between the second side of the second ear portion and the head when the band portion extends around the head, the second ear portion defining an opening; and a first membrane configured to be coupled to the first ear portion, when the first membrane is coupled to the first ear member the first membrane covering substantially an entirety of the opening of the first ear portion on the first side of the first ear portion and less than an entirety of the edge on the second side of the first ear portion;

a second membrane configured to be coupled the second ear portion when the second membrane is coupled to the second ear member the second membrane covering substantially an entirety of the opening of the second ear portion on the first side of the second ear portion and less than an entirety of the opening of the second ear portion on the second side of the second ear portion; and an attachment portion coupled to the second membrane, when the second membrane is coupled to the second ear portion, the attachment portion being directly coupled to at least a portion of a perimeter of the second ear portion.

21. The apparatus of claim 20, wherein the first membrane has an attachment portion configured to engage at least a portion of a perimeter of the first ear portion, the attachment portion of the first membrane configured to cover a portion of the second side of the first ear portion when the first membrane is coupled to the first ear portion.

22. The apparatus of claim 20, wherein the second membrane is configured to cover an area of the first side of the second ear portion and an area of the second side of the second ear portion smaller than the area of the first side of the second ear portion.

* * * * *